United States Patent [19]
Johnson et al.

[11] Patent Number: 5,702,637
[45] Date of Patent: Dec. 30, 1997

[54] LIQUID CRYSTAL COMPOUNDS HAVING A CHIRAL FLUORINATED TERMINAL PORTION

[75] Inventors: Gilbert C. Johnson, Lino Lakes; Marc D. Radcliffe, Woodbury; Patricia M. Savu, Maplewood; Daniel C. Snustad, Woodbury; Terence D. Spawn, West Lakeland Township, Washington County, all of Minn.

[73] Assignee: Minnesota Mining and Manufacturing Company, St. Paul, Minn.

[21] Appl. No.: 424,892

[22] Filed: Apr. 19, 1995

[51] Int. Cl.⁶ .......... C09K 19/34; C09K 19/32; C07C 25/13; C07D 239/02
[52] U.S. Cl. .......... 252/299.61; 252/299.62; 252/299.63; 544/303; 546/346; 549/380; 560/65; 570/129; 570/130; 570/144; 568/634; 568/649
[58] Field of Search .......... 252/299.01, 299.61, 252/299.62, 299.63; 544/30; 546/346; 549/380; 560/65; 568/634, 649; 570/127, 128, 129, 130, 131, 132, 133, 144

[56] References Cited

U.S. PATENT DOCUMENTS

| | | | |
|---|---|---|---|
| 2,519,983 | 8/1950 | Simons | 204/62 |
| 3,470,258 | 9/1969 | Tesoro | 260/615 |
| 4,001,137 | 1/1977 | Steinstrasser | 252/299 |
| 4,011,173 | 3/1977 | Steinstrasser | 252/299 |
| 4,113,647 | 9/1978 | Coates et al. | 252/299 |
| 4,202,791 | 5/1980 | Sato et al. | 252/299 |
| 4,256,656 | 3/1981 | Beguim et al. | 260/465 D |
| 4,330,426 | 5/1982 | Eidenschink et al. | 252/299.63 |
| 4,367,924 | 1/1983 | Clark et al. | 350/334 |
| 4,393,231 | 7/1983 | Misaki et al. | 560/73 |
| 4,400,293 | 8/1983 | Romer et al. | 252/299.63 |
| 4,411,494 | 10/1983 | Crossland et al. | 350/339 R |
| 4,419,664 | 12/1983 | Crossland et al. | 340/784 |
| 4,439,015 | 3/1984 | Rich et al. | 350/350 R |
| 4,481,149 | 11/1984 | Misaki et al. | 260/465 D |
| 4,528,562 | 7/1985 | Crossland et al. | 340/805 |
| 4,564,694 | 1/1986 | Hirai et al. | 560/1 |
| 4,572,794 | 2/1986 | Eidenschink et al. | 252/299.2 |
| 4,576,732 | 3/1986 | Isogai et al. | 252/299.65 |
| 4,592,858 | 6/1986 | Higuchi et al. | 252/299.66 |
| 4,613,209 | 9/1986 | Goodby et al. | 350/350 S |
| 4,614,608 | 9/1986 | Le Barny et al. | 252/299.64 |
| 4,617,140 | 10/1986 | Eidenschink et al. | 252/299.61 |
| 4,668,427 | 5/1987 | Saito et al. | 252/299.66 |
| 4,780,242 | 10/1988 | Miyazawa et al. | 252/299.65 |
| 4,816,178 | 3/1989 | Katagiri et al. | 252/299.6 |
| 4,816,596 | 3/1989 | Langlois | 358/423 |
| 4,837,364 | 6/1989 | Desbois et al. | 568/43 |
| 4,876,027 | 10/1989 | Yoshinaga et al. | 252/299.65 |
| 4,879,060 | 11/1989 | Shionozaki et al. | 252/299.61 |
| 4,886,619 | 12/1989 | Janulis | 252/299.1 |
| 4,914,224 | 4/1990 | Shoji et al. | 560/65 |
| 5,051,527 | 9/1991 | Suzuki et al. | 560/51 |
| 5,062,691 | 11/1991 | Tristani-Kendra et al. | 359/56 |
| 5,082,587 | 1/1992 | Janulis | 252/299.01 |
| 5,141,669 | 8/1992 | Bloom et al. | 252/299.65 |
| 5,167,859 | 12/1992 | Wachtler et al. | 252/299.61 |
| 5,194,179 | 3/1993 | Suzuki et al. | 252/299.66 |
| 5,252,695 | 10/1993 | Niciri et al. | 528/30 |
| 5,262,082 | 11/1993 | Janulis et al. | 252/299.01 |
| 5,362,919 | 11/1994 | Costello et al. | 568/601 |
| 5,377,033 | 12/1994 | Radcliffe | 359/75 |
| 5,399,291 | 3/1995 | Janulis et al. | 252/299.01 |
| 5,417,883 | 5/1995 | Epstein et al. | 252/299.01 |
| 5,474,705 | 12/1995 | Janulis et al. | 252/299.01 |
| 5,547,605 | 8/1996 | Fuss et al. | 252/299.6 |

FOREIGN PATENT DOCUMENTS

| | | | |
|---|---|---|---|
| 0 047 877 | 3/1982 | European Pat. Off. | C07C 103/375 |
| 0 163 229 | 12/1985 | European Pat. Off. | C09K 19/02 |
| 0 181 601 | 5/1986 | European Pat. Off. | C09K 19/60 |
| 0 255 236 | 2/1988 | European Pat. Off. | |
| 0 331 367 | 9/1989 | European Pat. Off. | |
| 0 332 025 | 9/1989 | European Pat. Off. | C07C 121/407 |
| 0 548 548 | 6/1993 | European Pat. Off. | G02F 1/137 |
| 0 641 850 | 3/1995 | European Pat. Off. | |
| 0 667 384 | 8/1995 | European Pat. Off. | |
| 33 32 692 | 3/1985 | Germany | C07C 121/46 |
| 40 34 123 | 4/1992 | Germany | C07C 19/08 |
| 43 08 028 | 9/1994 | Germany | |
| 44 44 701 | 6/1995 | Germany | |
| 57-165334 | 10/1982 | Japan | C07C 43/22 |
| 1-104031 | 4/1989 | Japan | C07C 69/63 |
| 2-69443 | 3/1990 | Japan | C07C 69/92 |
| 2 162 515 | 2/1986 | United Kingdom | C07C 69/773 |
| WO 88/03530 | 5/1988 | WIPO | C07D 239/26 |
| WO 88/05803 | 8/1988 | WIPO | C09K 19/52 |
| WO 88/08441 | 11/1988 | WIPO | C09K 19/30 |
| WO 91/00897 | 1/1991 | WIPO | C09K 19/34 |
| WO 91/11418 | 8/1991 | WIPO | C07C 22/08 |

OTHER PUBLICATIONS

Jajer et al., Synthesis 1990, 556.
Chaudhary et al., Tetrahedron Letters 1979, 95.
Middleton, J. Org. Chem. 40, 574 (1975).
Sakaguchi et al., Ferroelectrics 114, 265 (1991).
Byun et al, Tet. Lett. 30, 2751 (1989).
Gray et al., J. Chem. Soc., Perkin Trans. II 1989, 2041.
Iwakura et al., J. Org. Chem. 29, 379 (1964).
Miyasato et al., Jap. J. Appl. Phys. 22, L 661 (1983).
H. Nohira et al., Mol. Cryst. Liq. Cryst. 180B, 379–88 (1990).
"Antiferroelectric Chiral Smectic Liquid Crystals", Fukuda et al., J. Mater. Chem. 4 (7), 997 (1994).

(List continued on next page.)

*Primary Examiner*—Shean C. Wu
*Attorney, Agent, or Firm*—Gary L. Griswold; Walter N. Kirn; Lucy C. Weiss

[57] ABSTRACT

Fluorine-containing, chiral liquid crystal compounds comprise (a) a chiral fluorochemical terminal portion containing at least one methylene group and optionally containing at least one catenary ether oxygen atom; (b) a saturated, chiral or achiral, hydrocarbon terminal portion; and (c) a central core connecting the terminal portions. The compounds have smectic mesophases or latent smectic mesophases and are useful, for example, in liquid crystal display devices.

2 Claims, No Drawings

OTHER PUBLICATIONS

"Effect of Chiral End Group Variation on the Properties of Ferroelectric Copolymers", Naciri et al., Ferroelectrics 148, 297 (1993).

Pelzl et al., Kristall Technik. 14, 817 (1979).

Pelzl et al., Liquid Crystals 2, 131 (1987).

Sierra et al., J. Am. Chem. Soc. 114, 7645 (1992).

Meyer, R.B. et al., J. Physique 36, L–69 (1975).

Zaschke, H. and Stolle, R., "Synthese niedrigschmelzender Kristallin–Flussiger Hetercyclen; 5–n–Alkyl–2–[4–n–alkanoyloxy–phenyl]pyrimidine", Z. Chem. 15, 441–43 (1975).

Mochizuki, A. et al., SPIE 1665 108–09 (1992).

Pelzl, G. et al., Mol. Cryst. Liq Cryst. 53, 167 (1979).

Clark, N.A. et al., Appl. Phys. Lett. 36, 899 (1980).

Holy, A. and Z. Arnold, Collection Chzechoslov. Chem. Commun. 38, 1371 (1973).

Kahn, F.J., Appl. Phys. Lett. 22, 111 (1973).

Lagerwall et al., 1st International Symposium On Ferroelectric Liquid Crystals, Bordeaux–Arcachon, France, 1987.

Partridge, M.W., and W.F. Short, J. Chem. Soc., 390 (1947).

P.M. Savu, Kirk–Othmer Encyclopedia of Chemical Technology, Fourth Edition, vol. 11, pp. 558–564, John Wiley & Sons, New York (1994).

Knunyants, I.L., L. Chih–yuan and V.V. Shokina, Advances in Chem. (Usepkhi Khimi) 42, original 1502, Eng. Trans, 461–76 (1963) Translation RSIC–165 (Redstone Information Center).

Arnold, Z. and F. Sorm, Coll. Czech. Chem. Commun. 23, 452 (1958).

Abe, T., and S. Nagase, "Electrochemical Fluorination (Simons Process), as a Route to Perfluorinated Organic Compounds of Industrial Interest," Preparation, Properties and Industrial Applications of Organofluorine Compounds, 37–38 (1982).

Patent Abtracts of Japan vol. 15, No. 271 (C–0848), Jul. 10, 1991.

Molecular Crystals Liquid Crystals 47, 1 (1978).

Molecular Crystals Liquid Crystals 67, 235 (1981).

"The Silicon Liquid–Crystal Light Value", J. Appl. Phys. 57(4), 1356 (1985).

"Smectic Liquid Crystal from (Perfluorodecyl)decane", Molecular Crystals Liquid Crystals 2 (3–4), 111 (1985).

Molecular Crystals Liquid Crystals 114, 237 (1984).

J. Am. Chem. Soc. 86, 964 (1964).

Jap. Journal of Applied Physics 24(11), 1389 (1985).

J.W. Goodby and T.M. Leslie, "Some Novel Ferroelectric Smectic Liquid Crystals", Liquid Crystals & Ordered Fluids, vol. 4, pp. 1–32, Plenum Press, New York, (1984).

Gray, G.W., Liquid Crystals & Plastic Crystals, vol. 1, pp. 142–143, Ellis Horwood Limited (1974).

Zverkova, T.I. et al., Advances in Liquid Crystal Research & Applications, Pergamon Press, Oxford, pp. 991–995 (1980).

LeBarny, P. et al., Molecular Crystals and Liquid Crystals 127, 413 (1985).

Streitweiser, A. et al., Introduction to Organic Chemistry, pp. 378–380, 480, 837, Macmillan Publishing Co., New York (1976).

Sirutkaitis, R. et al., Advances in Liquid Crystal Research and Applications, Pergamon Press, Oxford, pp. 1023–1028 (1980).

Schiller et al., Liquid Crystals 2, 21 (1987).

LIQUID CRYSTAL COMPOUNDS HAVING A CHIRAL FLUORINATED TERMINAL PORTION

FIELD OF THE INVENTION

This invention relates to fluorinated chiral smectic liquid crystal compounds, to a process for the preparation of such compounds (and to intermediates for use therein), and to liquid crystal compound mixtures and electrooptical display devices containing such compounds.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available.

One of the most important characteristics of a liquid crystal display device is its response time, i.e., the time required for the device to switch from the on (light) state to the off (dark) state. In a ferroelectric or anti-ferroelectric device, response time ($\tau = \eta/P_s E$) is proportional to the rotational viscosity ($\eta$) of the liquid crystal compound(s) contained within the device and is inversely proportional to their polarization ($P_s$) and to the applied electric field (E). Thus, response time can be reduced by using compound(s) having high polarizations or low viscosities, and such compounds are greatly desired in the art. In addition to fast response times, compounds should ideally possess broad smectic temperature ranges to enable operation of the device over a broad range of temperatures (or should be capable of combination with other liquid crystal compounds having different smectic temperature ranges without adversely affecting the smectic phase behavior of the base mixture).

SUMMARY OF THE INVENTION

Briefly, in one aspect, this invention provides fluorine-containing, chiral liquid crystal compounds having smectic mesophases or latent smectic mesophases. (Compounds having latent smectic mesophases are those which by themselves do not exhibit a smectic mesophase, but which, when in admixture with compounds having smectic mesophases or with other compounds having latent smectic mesophases, develop smectic mesophases under appropriate conditions.) The chiral liquid crystal compounds of the invention comprise (a) a chiral fluorochemical terminal portion containing at least one methylene group and optionally containing at least one catenary, i.e., in-chain, ether oxygen atom; (b) a saturated, chiral or achiral, hydrocarbon terminal portion; and (c) a central core connecting the terminal portions. The chiral fluorochemical terminal portion can be represented by the formula —D—R*—D—(O)$_x$—CH$_2$—D'—R$_f$, where R* is a cyclic or acyclic chiral moiety; x is an integer of 0 or 1; R$_f$ is fluoroalkyl, perfluoroalkyl, fluoroether, or perfluoroether; and D' and each D are independently and non-directionally selected from the group consisting of a covalent bond,

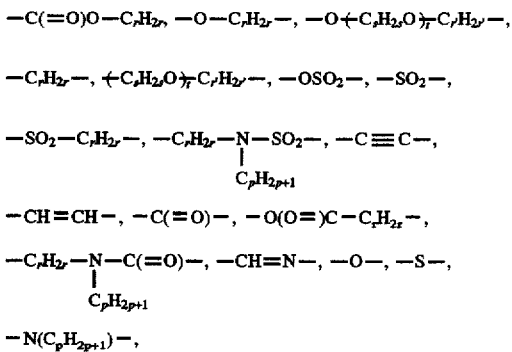

and combinations thereof, where r and r' are independently integers of 0 to about 20, s is independently an integer of 1 to about 10 for each (C$_s$H$_{2s}$O), t is an integer of 1 to about 6, and p is an integer of 0 to about 4. When the R$_f$ group of the fluorochemical terminal portion is perfluoroalkyl or perfluoroether, it can contain small amounts of residual carbon-bonded hydrogen atoms but is preferably completely fluorinated. Preferably, R$_f$ is fluoroalkyl, fluoroether, or perfluoroether; more preferably, R$_f$ is perfluoroether, as the perfluoroether-containing compounds of the invention exhibit, e.g., a broad smectic C mesophase, good compatibility with other smectic C compounds, and advantageous layer spacing behavior. D' is preferably a covalent bond.

In general, the compounds of this invention have a central core comprised of at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC=N—, —CH=CH—, —C≡C—, and —COSe—. The rings can be fused or non-fused. The heteroatoms within the heteroaromatic rings comprise at least one atom selected from the group consisting of nitrogen, oxygen, and sulfur. Non-adjacent ring carbon atoms in the alicyclic rings can be substituted by nitrogen, oxygen, or sulfur atoms. When the ring(s) are aromatic, heteroaromatic, substituted aromatic, or substituted heteroaromatic, the non-fused rings of the core are preferably no more than about two in number.

When used in electrooptical display devices, the chiral liquid crystal compounds of the invention provide exceptionally fast response times over broad temperature ranges. The compounds exhibit surprisingly high polarization values (relative to comparable compounds having a chiral center located on the other side of the core, away from the fluorochemical terminal portion) and surprisingly low viscosities in view of their high polarizations. In addition, many of the compounds have broad smectic C. temperature ranges, making them useful alone, as well as in admixture with other chiral or achiral liquid crystal compounds (as dopants or as the major components), for electrooptical display applications.

The compounds of the invention have a number of desirable properties when used in admixture with other liquid crystal compounds, preferably compounds having fluorinated terminal portions such as those compounds disclosed, for example, in U.S. Pat. No. 4,886,619 (Janulis), U.S. Pat. No. 5,082,587 (Janulis), and U.S. Pat. No. 5,262,082 (Janulis et al.). For example, the compounds of the invention when admixed with such preferred liquid crystal compounds show excellent compatibility, show a beneficial effect or only a minimal negative effect on the smectic C.

temperature range of the resulting mixtures (even when present at high concentrations), and provide ferroelectric mixtures having fast electrical response times.

In other aspects, this invention also provides a mixture of liquid crystal compounds comprising at least one liquid crystal compound of the invention, a liquid crystal display device containing at least one liquid crystal compound of the invention, liquid crystal intermediate compounds, and a process for preparing the liquid crystal compounds of the invention.

DETAILED DESCRIPTION OF THE INVENTION

A class of the non-polymeric liquid crystal materials, i.e., liquid crystal compounds, of the present invention can be represented by the general formula I:

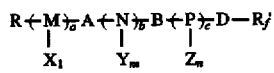  (I)

where M, N, and P are each independently selected from the group consisting of

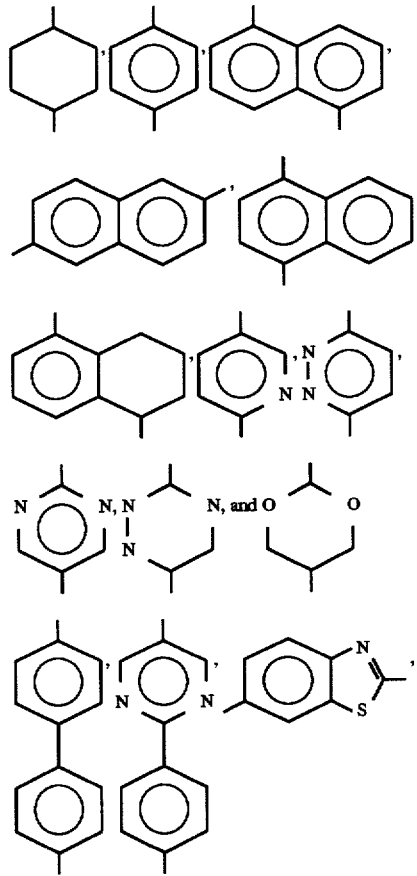

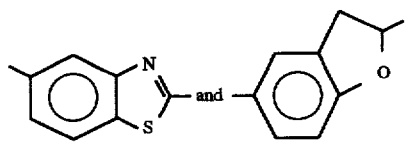

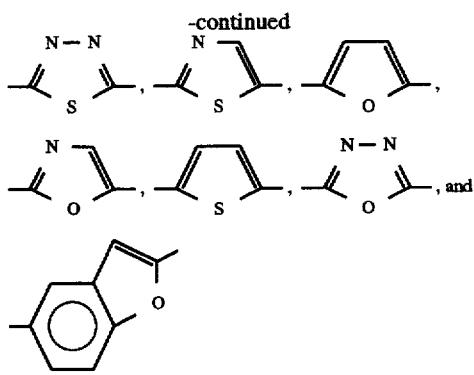

a, b, and c are each independently zero or an integer of from 1 to 3, with the proviso that the sum of a+b+c be at least 1 (and preferably no greater than 2);

each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

D is non-directionally selected from the group consisting of a covalent bond,

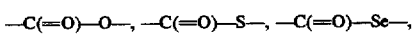

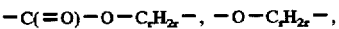

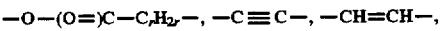

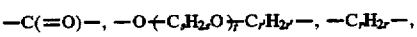

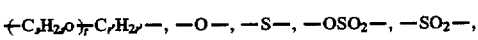

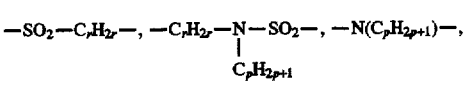

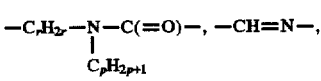

and combinations thereof, where r and r' are independently integers of 0 to about 20, s is independently an integer of 1 to about 10 for each (C$_s$H$_{2s}$O), t is an integer of 1 to about 6, and p is an integer of 0 to about 4;

R is selected from the group consisting of

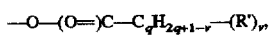

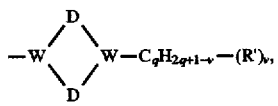

and

where each R' is independently selected from the group consisting of —Cl, —F, -CF$_3$, —NO$_2$, —CN, —H, —H$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$ (preferably, —H or —F); q' is independently an integer of 1 to about 20 for each (C$_q$H$_{2q}$—O); q is an integer of 1 to about 20; w is an integer of 0 to about 10; v is an integer of 0 to about 6; each v' is independently an integer of 0 to about 6; g is an integer of 1 to about 3; each D is independently and non-directionally selected from the group set forth for D above, with the proviso that the ring containing D has from about 3 to about 10 ring atoms; each W is independently selected from the group consisting of N, CR', and SiR'; and R can be chiral or achiral; and R$_f'$ is —R*—D—(O)$_x$—CH$_2$—D'—R$_f$, where R* is a cyclic or acyclic chiral moiety; D and D' are each independently and non-directionally selected from the group set forth for D above; x is an integer of 0 or 1; and R$_f$ is fluoroalkyl, perfluoroalkyl, fluoroether, or perfluoroether. Preferably, R$_f$ is fluoroalkyl, fluoroether, or perfluoroether; and R* is selected from the group consisting of —O—((C$_q$H$_{2q'-v'}$—(R')$_{v'}$)—O)$_w$—C$_q$H$_{2q-v}$—(R')$_v$—, —((C$_q$H$_{2q'-v'}$—(R')$_{v'}$)—O)$_w$—C$_q$H$_{2q-v}$—(R')$_v$—, —C(=O)—O—C$_q$H$_{2q-v}$—(R')$_v$—, —O—(O=)C—C$_q$H$_{2q-v}$—(R')$_v$—,

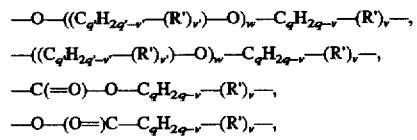, and —CR'H—(D)$_g$—CR'H—, where each R' is independently selected from the group consisting of —Cl, —F, —Cf$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$, (preferably, —H, —F, —CF$_3$, —Br, —OH, or —OCH$_3$; more preferably, —H, —F, or —CF$_3$); q' is independently an integer of 1 to about 20 for each ((C$_q$H$_{2q'-v'}$—(R')$_{v'}$)—O); q is an integer of 1 to about 20; w is an integer of 0 to about 10; v is an integer of 0 to about 6; each v' is independently an integer of 0 to about 6; g is an integer of 1 to about 3; each D is independently and non-directionally selected from the group set forth for D above, with the proviso that the ring containing D has from about 3 to about 10 ring atoms; and each W is independently selected from the group consisting of N, CR', and SiR'. More preferably, R$_f$ is perfluoroether. D' is preferably a covalent bond.

In defining R$_f$, particularly preferred perfluoroalkyl groups are those which can be represented by the formula —C$_q$F$_{2q}$X', where q is as defined above (and, preferably, is at least about 5) and X' is hydrogen or fluorine. Particularly preferred fluoroalkyl and fluoroether groups are those which can be represented by the formula —R$_f''$—R$_h$, where R$_f''$ is a linear or branched, perfluorinated or partially-fluorinated alkylene group having from 1 to about 10 (preferably, from about 2 to about 6) carbon atoms and optionally containing one or more catenary, i.e., in-chain, ether oxygen atoms, and R$_h$ is a linear or branched alkyl group having from 1 to about 14 (preferably, from about 3 to about 10) carbon atoms and optionally containing one or more catenary ether oxygen atoms. Preferably, R$_f''$ is perfluorinated, both R$_h$ and R$_f''$ are linear, and at least one of the groups R$_h$ and R$_f''$ contains at least one catenary ether oxygen atom. More preferably, R$_h$ or both R$_h$ and R$_f''$ contains at least one catenary ether oxygen atom.

Particularly preferred perfluoroether groups are those which can be represented by the formula —(C$_x$F$_{2x}$O)$_z$C$_y$F$_{2y+1}$, where x is independently an integer of 1 to about 10 for each (C$_x$F$_{2x}$O), y is an integer of 1 to about 10, and z is an integer of 1 to about 10. Preferably, the perfluoroether group is linear, x is independently an integer of 1 to about 6 for each (C$_x$F$_{2x}$O), y is an integer of 1 to about 6, and z is an integer of 1 to about 6.

Preferred subclasses of the chiral compounds of the invention can be represented by the following formula:

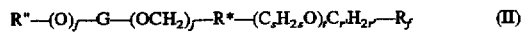 (II)

where R'' is (R')$_v$—C$_q$H$_{2q+1-v}$, where q is an integer of 2 to about 10, each R' is independently selected from the group consisting of hydrogen, fluorine, chlorine, methyl, and perfluoromethyl, and v is an integer of 1 to about 3; j is an integer of 0 or 1; G is selected from the group consisting of

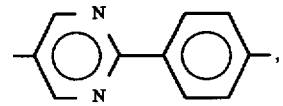,

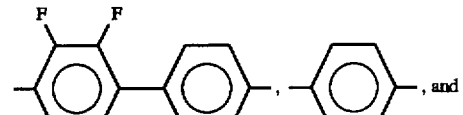, and

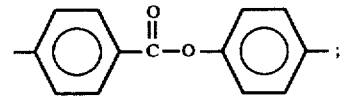;

R* is selected from the group consisting of —C$_q$H$_{2q-v}$—(R')$_v$— and

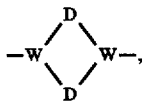, where R' is —F, q is an integer of 1 to about 4, v is an integer of 1 to about 3, W is N or CH, and D is —C(=O)—O— or —CH$_2$—; s is an integer of 1 to about 6; t is an integer of 0 or 1; r' is an integer of 1 to about 3; and R$_f$ is selected from the group consisting of —C$_q$F$_{2q}$X', —R$_f''$R$_h$, and —(C$_x$F$_{2x}$O)$_z$C$_y$F$_{2y+1}$, where q is an integer of 1 to about 6, X' is fluorine, R$_f''$ is a linear or branched, perfluorinated alkylene group having from about 2 to about 4 carbon atoms and optionally containing one or more catenary ether oxygen atoms, $R_h$ is a linear or branched alkyl group having from about 2 to about 7 carbon atoms and optionally containing one or more catenary ether oxygen atoms, x is independently an integer of 1 to about 10 for each ($C_xF_{2x}O$), y is an integer of 1 to about 8, and z is an integer of 1 to about 5.

The fluorine-containing liquid crystal compounds of the invention can be prepared by a process comprising the steps of (a) mixing at least one compound represented by the formula

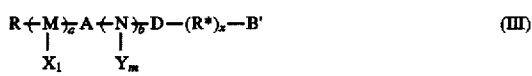 (III)

with at least one compound represented by the formula

 (IV)

or mixing at least one compound represented by the formula

 (V)

with at least one compound represented by the formula

 (VI)

or mixing at least one compound represented by the formula

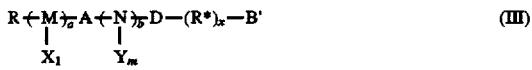 (III)

with at least one compound represented by the formula

 (VII)

where M, N, P, a, b, c, A, B, X, Y, Z, 1, m, n, D, R, R*, $R_f$, and $R_f'$ are as defined above for formula I; x is an integer of 0 or 1; and each A', A", B', and B" are independently selected from the group consisting of —H, —Cl, —Br, —I, —OH, —COOH, —CH(CH$_2$OH)$_2$, —SH, —SeH, —TeH, —NH$_2$, —COCl, —CHO, —OSO$_2$R$_f$''', —OSO$_2$CH$_3$, —NH(C=O)OC$_q$H$_{2q+1}$, —NCO, —OSO$_2$-cyclo(C$_6$H$_4$)—CH$_3$, —CH$_3$COOH, and —CH(C(O)O—C$_q$H$_{2q+1}$)$_2$, where $R_f'''$ is a perfluoroalkyl group having from 1 to about 10 carbon atoms and q is an integer of 0 to about 20, and with the proviso that (R*)$_x$—A' can enter into an addition or condensation reaction with A" and that (R*)$_x$—B' can enter into an addition or condensation reaction with B"; and (b) allowing compounds III and IV, compounds V and VI, or compounds III and VII to react, optionally in the presence of suitable coupling agent(s), i.e., reagent(s) which effect coupling.

Most of the compounds of the present invention have enhanced smectic mesophases. Mixtures of the compounds of the invention with other liquid crystal materials can be formulated to provide desired transition temperatures and broad mesophase temperature ranges. Such mixtures preferably contain compounds having fluorinated terminal portions, such as those compounds described, for example, in U.S. Pat. No. 4,886,619 (Janulis), U.S. Pat. No. 5,082,587 (Janulis), and, most preferably, U.S. Pat. No. 5,262,082 (Janulis et al.), the descriptions of which are incorporated herein by reference.

The compounds of this invention in admixture with other chiral or achiral liquid crystal compounds may exhibit chiral smectic liquid crystal behavior. Furthermore, many of the perfluoroether group-containing liquid crystal compounds of the invention when used alone or when mixed with other liquid crystal compounds of the invention or with achiral, fluorine-containing liquid crystal compounds (preferably, the perfluoroether group-containing liquid crystal compounds described in U.S. Pat. No. 5,262,082 (Janulis et al.)) exhibit a reduced temperature dependence of the smectic interlayer spacing. This property provides for the spontaneous generation of a bookshelf type layer structure, which is ideal for a ferroelectric liquid crystal device.

Another advantage of using the materials of this invention in the formulation of liquid crystal mixtures is the low birefringence which can be obtained. The low birefringence of the liquid crystal compounds of the invention (relative to their nonfluorine-containing analoques) allows the fabrication of devices with larger device spacings. Light transmission through, e.g., a surface-stabilized ferroelectric device (as described in U.S. Pat. No. 4,367,924, the description of which is incorporated by reference herein) with two polarizers is represented by the following equation:

$$I = I_o (\sin^2 (4\Theta)) (\sin^2 (\pi \Delta nd/\lambda))$$

where
$I_o$=transmission through parallel polarizers
$\Theta$=material tilt angle
$\Delta n$=liquid crystal birefringence
$d$=device spacing
$\lambda$=wavelength of light used To maximize the transmission, both $\sin^2(4\Theta)$ and $\sin^2(\pi\Delta nd/\lambda)$ must be at maximum. This occurs when each term equals one. The first term is a maximum when the tilt angle equals 22.5°. This is a function of the liquid crystal and is constant for a given material at a given temperature. The second term is maximum when $\Delta nd=\lambda/2$. This demonstrates the criticality of the low birefringence of the materials of this invention. Low birefringence allows a larger device thickness, d, for a given wavelength of light. Thus, a larger device spacing is possible while still maximizing transmission, allowing easier device construction.

Objects and advantages of this invention are further illustrated by the following examples, but the particular materials and amounts thereof recited in these examples, as well as other conditions and details, should not be construed to unduly limit this invention.

In the following examples, all temperatures are in degrees Celsius and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and nonfluorine-containing reactants to provide the precursor compounds, which, in turn, were caused to react together to yield the chiral, fluorine-containing liquid crystal compounds of this invention.

Compounds prepared in the various examples of this invention were characterized by their melting or boiling point, and structures were confirmed by using at least one of the following methods of analysis: chromatography; $^{13}$C—, $^1$H—, and $^{19}$F-NMR; and infrared and mass spectroscopies.

EXAMPLES

The 5-alkyl-2-(4-hydroxyphenyl)pyrimidines used in the examples were prepared essentially as described by Zaschke and Stolle in "Synthese niedrigschmelzender Kristallin-Flussiger Heterocyclen; 5-n-Alkyl-2-[4-n-alkanoyloxy-phenyl]pyrimidine," Z. Chem. 15, 441–3 (1975). (S)- and (R)-2-fluoro-decyl-p-toluenesulfonate were prepared essentially as described by Nohira et al. in Mol. Cryst. Liq. Cryst. 180B, 379 (1990). Fluorinated alcohols were prepared essentially as described in U.S. Pat. No. 5,262,082 (Janulis et al.; the description of which is incorporated herein by reference) by sodium borohydride reduction of the corresponding perfluorinated acids (or derivatives), which had been prepared by electrochemical fluorination (ECF) or by direct fluorination (using elemental fluorine) of the corresponding hydrocarbon acids (or derivatives). See, e.g., the description of ECF given in U.S. Pat. No. 2,519,983 (Simons), the description of which is incorporated herein by reference. Direct fluorination is described, e.g., in U.S. Pat. No. 5,362,919 (Costello et al.), the description of which is also incorporated herein by reference.

Examples 1–35 describe procedures for preparing liquid crystal compounds and liquid crystal intermediate compounds of this invention. The chemical structure of each compound is given in Table 1.

Example 1

Preparation of 5-Octyl-2-[4-((R)-2-fluoro-5,5,6,6,7,7,8,8,9,9,10,10,10-tridecafluorodecyloxy)phenyl]pyrimidine Dry nitrogen was bubbled through a solution of (S)-1,2-O-isopropylidine-3-butene-1,2-diol (1.0 g, 7.8 mmol) (prepared essentially by the procedure of Jajer et al. described in Synthesis 1990, 556) and 1-iodoperfluorohexane (3.48 g, 7.8 mmol) for 10 minutes. Tetrakis(triphenylphosphine)palladium(0) (90 mg, 0.078 mmol) was added to the resulting mixture, and the mixture was stirred at room temperature for 10 hours. Tributyl tin hydride (2.1 ml, 7.8 mmol) was then added by syringe, and the mixture was stirred for an additional 10 hours. The resulting product was distilled (44° C., 0.4 mm Hg) from the mixture to give 2.5 g of (S)-1,2-O-isopropylidene-3-(perfluorohexyl)butane diol as a clear liquid. The dioxolane protecting group was then hydrolyzed to the diol by stirring the product in a solution of aqueous acidic tetrahydrofuran for 4 hours. The resulting product was distilled under reduced pressure (80°–85° C., 0.4 mmHg) to give 2.1 g of (S)-2-hydroxy-5,5,6,6,7,7,8,8,9,9,10,10,10-tridecafluoro-1-decanol. The primary alcohol was protected with trityl chloride (triphenylmethyl chloride) essentially as described by Chaudhary et al. in Tetrahedron Letters 1979, 95, and the resulting secondary alcohol was subsequently treated with diethylaminosulfur trifluoride (essentially as described by Middleton in J. Org. Chem. 40, 574 (1975)) to give triphenylmethoxy-(R)-2-fluoro-5,5,6,6,7,7,8,8,9,9,10,10,10-tridecafluorodecane. The trityl protecting group was then removed with aqueous acidic tetrahydrofuran to give (R)-2-fluoro-5,5,6,6,7,7,8,8,9,9,10,10,10-tridecafluoro-1-decanol. The p-toluene sulfonate derivative of the alcohol was prepared by the addition of 4-toluenesulfonyl chloride (120.6 mg, 0.63 mmol) to a solution of the alcohol (236 mg, 0.57 mmol), dimethylaminopyridine (DMAP, 2.8 mg, 0.02 mmol), and N,N'-diisopropylethylamine (0.2 ml, 1.14 mmol) in dichloromethane (2.0 ml). The resulting mixture was stirred for 8 hours at room temperature and was then coated onto 0.5 g of silica gel. The resulting product was then purified by eluting with 10:1 hexanes/ethyl acetate on silica to give 280 mg of the sulfonate.

Sodium hydride (30 mg, 60 weight percent in oil, 6.6 mmol) was added to a stirred solution of 5-octyl-2-(4-hydroxyphenyl)pyrimidine (169 mg, 0.59 mmol) and dimethyl formamide (2.0 ml). The resulting mixture was stirred for 15 minutes under a nitrogen atmosphere, and then a solution of the above-described sulfonate (280 mg, 0.496 mmol) in 2 ml of dimethyl formamide was added by syringe. The mixture was heated to 60° C. for 4 hours and then cooled to ambient temperature. The mixture was diluted with water (5 ml) and extracted with three 10 ml aliquots of diethyl ether. The organic extract were collected, dried (over MgSO$_4$), filtered, and concentrated to give product in the form of a brown paste which solidified upon standing. The product was then purified by column chromatography on silica gel (eluting with 10:1 hexanes/ethyl acetate) to give 233 mg of the title compound (having the structure shown in Table 1) as a white solid.

Example 2

Preparation of 5-Octyl-2-[4-((R)-2-fluoro-3-(2,2,3,3,4,4,5,5,6,6,6-undecafluorohexyloxy)propoxy)phenyl]pyrimidine (S)-2-hydroxy-3-(2,2,3,3,4,4,5,5,6,6,6-undecafluorohexyloxy)-propanol was prepared by the following modification of a procedure described in U.S. Pat. No. 3,470,258 (Teroso et al.). (R)-glycidol (5.0 g, 67.5 mmol) was added dropwise to a 120° C. solution of 2,2,3,3,4,4,5,5,6,6,6-undecafluorohexanol (30 g, 101 mmol) and N,N'-diisopropylethylamine (0.47 ml, 2.7 mmol). The resulting mixture was then stirred for one hour. The resulting product was distilled (79°–81° C. at 0.4 mm Hg) from the mixture to give 14.7 g of (S)-2-hydroxy-3-(2,2,3,3,4,4,5,5,6,6,6-undecafluorohexyloxy)-1-propanol as a clear liquid. (R)-2-fluoro-3-(2,2,3,3,4,4,5,5,6,6,6-undecafluorohexane-1-p-toluenesulfonate was then prepared using essentially the procedure described in Example 1.

Sodium hydride (0.223 g, 9.3 mmol) was added to a stirred solution of the sulfonate (3.00 g, 5.65 mmol) and 5-octyl-2-(4-hydroxyphenyl)pyrimidine (1.77 g, 6.2 mmoles) using essentially the procedure described in Example 1 to give the title compound.

Example 3

Preparation of 5-Octyl-2-[4-((R)-2-hydroxy-3-(2-(2-(nonafluorobutoxy)tetrafluoroethoxy)-2,2,-difluoroethoxy)propoxy)phenyl]pyrimidine A solution of potassium hydroxide (1.97 g, 35 mmol) in water (1.97 ml) was added to a solution of (R)-5-octyl-2-[4-(2,3-oxiranylpropoxy)phenyl]pyrimidine (10.0 g, 29.3 mmol) (prepared essentially as described by Sakaguchi et al. in Ferroelectrics 114, 269 (1992)), 2,2-difluoro-2-[1,1,2,2-tetrafluoro-2-nonfluorobutoxy)ethanol] (15.2 g, 35.16 mmol), and tetrabutyl ammonium hydrogen sulfate (500 mg, 1.5 mmol) in tetrahydrofuran (20 ml). The resulting mixture was heated to reflux temperature for 23 hours, was diluted with water (100 ml), and was extracted with three 100 ml aliquots of ethyl acetate. The organic extracts were concentrated under reduced pressure, and the resulting product was recrystallized from acetonitrile (150 ml) to give -2-[4-((R)-2-hydroxy-3-(2-(2-(nonafluorobutoxy)1,1,2,2-tetrafluoroethoxy)-2,2,-difluoroethoxy)propoxy)phenyl]-5-octyl-pyrimidine as a white solid.

Example 4

Preparation of 5-Octyl-2-[4-((S)-2-fluoro-3-(2-(2-(nonafluorobutoxy)tetrafluoroethoxy)-2,2,-difluoroethoxy)propoxy)phenyl]pyrimidine A solution of 5-octyl-2-[4-((R)-2-hydroxy-3-(2-(2-(nonafluorobutoxy)tetrafluoroethoxy)-2,2,-difluoroethoxy)

propoxy)phenyl]pyrimidine (prepared essentially as in Example 3, 8.0 g, 10.35 mmol) in dry tetrahydrofuran (50 ml) was added dropwise to a −70° C. solution of diethylaminosulfur trifluoride (3.3 g, 20.7 mmol) in tetrahydrofuran (50 ml). The resulting mixture was warmed to −30° C. over a period of 2 hours, and then pyridine (3.3 g, 41.4 mmol) was added to the mixture. The mixture was allowed to warm to ambient temperature and was stirred for 12 hours. The mixture was then poured into a slurry of silica gel (40 g) in diethyl ether and was concentrated onto the silica gel under reduced pressure. The product-coated silica was placed on top of 100 g of fresh silica gel and was eluted with a 10:1 hexanes/ethyl acetate solution. Fractions collected containing the product were concentrated under reduced pressure. The product was then recrystallized from methanol to give 4.9 g of the title compound as a white solid.

Example 5

Preparation of 5-Octyl-2-[4-((R)-2-fluoro-3-(2-(2-(nonafluorobutoxy)tetrafluoroethoxy)-2,2,-difluoroethoxy)propoxy)phenyl]pyrimidine The title compound was prepared essentially as described in Example 4 using 5-octyl-2-[4-((S)-2-hydroxy-3-(2-(2-(nonafluorobutoxy)tetrafluoroethoxy)-2,2,-difluoroethoxy)propoxy)phenyl]pyrimidine in place of 5-octyl-2-[4-((R)-2-hydroxy-3-(2-(2-(nonafluorobutoxy)tetrafluoroethoxy)-2,2,-difluoroethoxy)propoxy)phenyl]pyrimidine.

Example 6

Preparation of 5-Octyl-2-[4-((S)-2-bromo-3-(2-(2-(nonafluorobutoxy)tetrafluoroethoxy)-2,2,-difluoroethoxy)propoxy)phenyl]pyrimidine Perfluorobutanesulfonyl fluoride (389 mg, 1.29 mmol) was added dropwise to a −20° C. solution of 5-octyl-2-[4-((R)-2-hydroxy-3-(2-(2-(nonafluorobutoxy)tetrafluoroethoxy)-2,2, -difluoroethoxy)propoxy)phenyl]pyrimidine (Example 4, 1.0 g, 1.29 mmol) and diisopropyl ethylamine (334 mg, 2.58 mmol) in tetrahydrofuran (2 ml). Tetrabutylammonium bromide (416 mg, 1.29 mmol) was then added to the resulting mixture, and the mixture was allowed to warm to ambient temperature. The mixture was stirred at ambient temperature for 5 hours. The mixture was coated on to silica gel, and the resulting product was then purified by column chromatography (eluting with 10:1 hexanes/ethyl acetate) followed by recrystallization from methanol.

Example 7

Preparation of 5-Octyl-2-[4-((R)-2-methoxy-3-(2-(2-(nonafluorobutoxy)tetrafluoroethoxy)-2,2,-difluoroethoxy)propoxy)phenyl]pyrimidine Methyl iodide (1.1 g, 7.76 mmol) was added to a solution of 5-octyl-2-[4-((R)-2-hydroxy-3-(2-(2-(nonafluorobutoxy)tetrafluoroethoxy)-2,2,-difluoroethoxy)propoxy)phenyl]pyrimidine (Example 4, 1.5 g, 1.94 mmol) and sodium hydride (116 mg, 60 weight percent in oil, 2.91 mmol) in dimethyl formamide (10 ml). The resulting mixture was stirred at room temperature for 10 hours, was diluted with 50 ml of water, and was extracted with three 50 ml aliquots of diethyl ether. The organic extracts were dried (over $MgSO_4$), filtered, and concentrated. The resulting product was then recrystallized from methanol at −30° C. to give a white smectic material.

Example 8

Preparation of 5-Hexyl-2-[4-((R)-2-fluoro-3-(2-(2-(nonafluorobutoxy)tetrafluoroethoxy)-2,2,-difluoroethoxy)propoxy)phenyl]pyrimidine A solution of 5-hexyl-2-(4-hydroxyphenyl)pyrimidine (1.0 g, 4.08 mmol), 3-(2-[2-(nonafluorobutoxy) tetrafluoroethoxy]-2,2-difluoroethoxy)-(R)-2-fluoropropyl-1-p-toluenesulfonate (2.7 g, 4.08 mmol, prepared essentially as described in Example 2 by replacing 2,2,3,3,4,4,5,5,6,6, 6-undecafluorohexanol with 2-[2-(nonafluorobutoxy) tetrafluoroethoxy]-2,2-difluoro-1-ethanol), and potassium carbonate (0.62 g, 4.5 mmol) in acetonitrile (30 ml) was heated to reflux temperature and maintained at that temperature for 16 hours. The resulting mixture was then coated onto silica gel, and the resulting product was purified by column chromatography and subsequent recrystallization from methanol.

Example 9

Preparation of 5-Hexyloxy-2-[4-((R)-2-fluoro-3-(2-(2-(nonafluorobutoxy)tetrafluoroethoxy)-2,2,-difluoroethoxy)propoxy)phenyl]pyrimidine 2-Hexyloxyacetaldehyde diethylacetal was prepared as follows:

Hexanol (200 g, 1.96 mol) and toluene (600 ml) were added to a 3 liter flask fitted with a mechanical stirrer and a reflux condenser. Sodium hydride (51.6 g, 2.15 mol) was added slowly to the resulting mixture, and then bromoacetaldehyde diethylacetal (385.7 g, 1.96 mol) was added dropwise. The mixture was heated to reflux temperature and maintained at that temperature for 6 hours. The mixture was then cooled to ambient temperature and was filtered to remove the resulting solids. Toluene was removed from the filtrate under reduced pressure, and the resulting product was distilled (85°–88° C.) to give 189.4 g of 2-hexyloxyacetaldehyde diethylacetal.

5-Hexyloxy-2-(4-hydroxyphenyl)pyrimidine was prepared essentially by the procedure described by Zaschke et al., supra. The title compound was then prepared essentially as described in Example 8 by replacing 5-hexyl-2-(4-hydroxyphenyl)pyrimidine with 5-hexyloxy-2-(4-hydroxyphenyl)pyrimidine (0.54 g, 2.0 mmol).

Example 10

Preparation of 5-Octyloxy-2-[4-((R)-2-fluoro-3-(2-(2-(nonafluorobutoxy)tetrafluoroethoxy)-2,2,-difluoroethoxy)propoxy)phenyl]pyrimidine 5-Octyloxy-2-(4-hydroxyphenyl)pyrimidine was prepared essentially as described in Example 9 by substituting octanol for hexanol. The title compound was then prepared essentially as described in Examples 3 and 4 by replacing (R)-5-octyl-2-[4-(2,3-oxiranylpropoxy)phenyl]pyrimidine with (S)-5-octyloxy-2-[4-(2,3-oxiranylpropoxy)phenyl] pyrimidine (10.0 g, 28.0 mmol) and using 2-[2-(nonfluorobutoxy)tetrafluoroethoxy]-2,2-difluoroethanol (13.3 g, 31 mmol). The resulting (S)-hydroxy compound was treated with 2 equivalents of diethylaminosulfur trifluoride to produce the title compound.

Example 11

Preparation of 5-Octyl-2-[4-((R)-2-fluoro-3-(2-(2-(2-(trifluoromethoxy)tetrafluoroethoxy) tetrafluoroethoxy)-2,2,-difluoroethoxy)propoxy) phenyl]pyrimidine The title compound was prepared essentially as described in Examples 3 and 4 by combining 2-(2-(2-

(trifluoromethoxy)tetrafluoroethoxy)tetrafluoroethoxy)-2,2-difluoro-1-ethanol (2.8 g, 7.0 mmol) with (S)-5-octyl-2-[4-(2,3-oxiranylpropoxy)phenyl]pyrimidine (2.0 g, 5.87 mmol) to produce 5-octyl-2-[4-((S)-2-hydroxy-3-(2-(2-(2-(trifluoromethoxy)tetrafluoroethoxy)tetrafluoroethoxy)-2,2,-difluoroethoxy)propoxy)phenyl]pyrimidine. This chiral (S)-hydroxy compound (2.95 g, 4.0 mmol) was treated with diethylaminosulfur trifluoride (1.29 g, 8.0 mmol) to produce the title compound.

Example 12

Preparation of 5-Octyl-2-[4-((S)-2-fluoro-3-(4-(nonafluorobutoxy)-2,2,3,3,4,4-hexafluorobutoxy)propoxy)phenyl]pyrimidine (R)-Benzylglycidyl ether (2.0 g, 12.2 mmol, prepared essentially as described by Byun et al. in Tet. Lett. 30, 2751 (1989)) was added dropwise to a 120° C. solution of potassium carbonate (0.17 g, 1.2 mmol) in 4-nonafluorobutoxy-2,2,3,3,4,4-hexafluoro-1-butanol (5.1 g, 12.2mmol). The resulting mixture was stirred for 3 hours at 120° C. and was then cooled to ambient temperature and distilled (0.6 torr, 110°–130° C.) to give 6.25 g of 1-benzyloxy-(R)-2-hydroxy-3-(4-(nonafluorobutoxy)-2,2,3,3,4,4-hexafluorobutoxy)propane.

This product was then converted to 1-benzyloxy-(S)-2-fluoro-3-(4-nonafluorobutoxy-2,2,3,3,4,4-hexafluorobutoxy)propane by essentially the procedure described in Example 4. Removal of the benzyl protecting group was effected by hydrogenation (3100 torr (60 psi) $H_2$ and a catalytic amount of 10% Pd on carbon in tetrahydrofuran) to give (S)-2-fluoro-3-(4-nonafluorobutoxy-2,2,3,3,4,4-hexafluorobutoxy)-1-propanol.

(S)-2-fluoro-3-(4-(nonafluorobutoxy)-2,2,3,3,4,4-hexafluorobutoxy)propyl-1-p-toluenesulfonate was prepared essentially as described in Example 1. The title compound was then prepared essentially as described in Example 8 using 5-octyl-2-(4-hydroxyphenyl)pyrimidine (1.5 g, 5.28 mmol) and (S)-2-fluoro-3-(4-(nonafluorobutoxy)-2,2,3,3,4,4-hexafluorobutoxy)propyl-1-p-toluenesulfonate (3.1 g, 4.8 mmol).

Example 13

Preparation of 5-Octyl-2-[4-((R)-2-fluoro-3-(10-(2-(nonafluorobutoxy)tetrafluoroethoxy)-2,2,3,3,4,4,5,5,6,6,7,7,8,8,9,9,10,10-octadecafluorodecyloxy)propoxy)phenyl]pyrimidine The title compound was prepared essentially as described in Examples 3 and 4 by combining 10-(2-(nonafluorobutoxy)tetrafluoroethoxy)-2,2,3,3,4,4,5,5,6,6,7,7,8,8,9,9,10,10-octadecafluoro-1-decanol (5.8 g, 7.0 mmol) with (S)-5-octyl-2-[4-(2,3-oxiranylpropoxy)phenyl]pyrimidine (2.0 g, 5.87 mmol) to produce 5-octyl-2-[4-((S)-2-hydroxy-3-(10-(2-(nonafluorobutoxy)tetrafluoroethoxy)-2,2,3,3,4,4,5,5,6,6,7,7,8,8,9,9,10,10-octadecafluorodecyloxy)propoxy)phenyl]pyrimidine. This chiral (S)-hydroxy compound (3.6 g, 3.1 mmol) was treated with diethylaminosulfur trifluoride (1.0 g, 6.2 mmol) to produce the title compound.

Example 14

Preparation of 5-Octyl-2-[4-((R)-2-fluoro-3-(5-butoxy-2,2,3,3,4,4-hexafluoropentoxy)propoxy)phenyl]pyrimidine The title compound was prepared essentially as described in Examples 3 and 4 by combining 5-butoxy-2,2,3,3,4,4-hexafluoropentanol (3.1 g, 11.7 mmol, prepared essentially by the method described in U.S. Pat. No. 5,399,291 (Janulis et al.)) with (S)-5-octyl-2-[4-(2,3-oxiranylpropoxy)phenyl]pyrimidine (2.0 g, 5.87 mmol) to produce 5-octyl-2-[4-((S)-2-hydroxy-3-(-5-butoxy-2,2,3,3,4,4-hexafluoropentoxy)propoxy)phenyl]pyrimidine. This chiral (S)-hydroxy compound (2.0 g, 3.3 mmol) was treated with diethylaminosulfur trifluoride (1.06 g, 6.6 mmol) to produce the title compound.

Example 15

Preparation of 5-Octyl-2-[4-((R)-2-fluoro-3-(2-(N-(2,2,3,3,5,5,6,6-octafluoro)morpholino)-2,2-difluoroethoxy)propoxy)phenyl]pyrimidine The title compound was prepared essentially as described in Examples 3 and 4 by combining 2-(N-(2,2,3,3,5,5,6,6-octafluoro)morpholino)-2,2-difluoroethanol (2.18 g, 7.0 mmol) with (S)-5-octyl-2-[4-(2,3-oxiranylpropoxy)phenyl]pyrimidine (2.0 g, 5.87 mmol) to produce 5-octyl-2-[4-((S)-2-hydroxy-3-(2-(N-(2,2,3,3,5,5,6,6-octafluoro)morpholino)-2,2-difluoroethoxy)propoxy)phenyl]pyrimidine. This chiral (S)-hydroxy compound (3.0 g, 4.6 mmol) was treated with diethylaminosulfur trifluoride (1.5 g, 9.2 mmol) to produce the title compound.

Example 16

Preparation of 5-Octyl-2-[4-((R)-2-fluoro-3-(2-(2-(2-(nonafluorobutoxy)tetrafluoroethoxy)-2,2,-difluoroethoxy)ethoxy)propoxy)phenyl]pyrimidine The title compound was prepared essentially as described in Examples 3 and 4 by combining 2-(2-(2-(nonafluorobutoxy)tetrafluoroethoxy)-2,2,-difluoroethoxy)ethanol (3.3 g, 7.0 mmol) with (S)-5-octyl-2-[4-(2,3-oxiranylpropoxy)phenyl]pyrimidine (2.0 g, 5.87 mmol) to produce 5-octyl-2-[4-((S)-2-hydroxy-3-(2-(2-(2-(nonafluorobutoxy)tetrafluoroethoxy)-2,2,-difluoroethoxy)ethoxy)propoxy)phenyl]pyrimidine. This chiral (S)-hydroxy compound (1.6 g, 1.95 mmol) was treated with diethylaminosulfur trifluoride (0.63 g, 3.92 mmol) to produce the title compound.

Example 17

Preparation of (R)-2,3-Difluoro-4-octyl-4'-(2-fluoro-3-(2-(2-(nonafluorobutoxy)tetrafluoroethoxy)-2,2,-difluoroethoxy)propoxy)1,1'-biphenyl The title compound was prepared essentially as described in Example 8 by combining 3-(2-[2-(nonfluorobutoxy)tetrafluoroethoxy]-2,2-difluoroethoxy)-(R)-2-fluoropropyl-1-p-toluenesulfonate (0.5 g, 0.75 mmol) with 2,3-difluoro-4-octyl-4'-hydroxybiphenyl (0.24 g, 0.75 mmol, prepared essentially as described by Gray et al. in J. Chem. Soc., Perkin Trans. II 1989, 2041).

Example 18

Preparation of 5-((R)-2-Fluorodecyloxy)-2-[4-((R)-2-fluoro-3-(2-(2-(nonafluorobutoxy)tetrafluoroethoxy)-2,2,-difluoroethoxy)propoxy)phenyl]pyrimidine 5-Benzyloxy-2-(4-hydroxy)phenyl]pyrimidine was prepared essentially as described in Example 9 by replacing benzyl alcohol for hexanol. 5-Benzyloxy-2-(4-((R)-2-fluoro-3-(2-(2-(nonafluorobutoxy)tetrafluoroethoxy)-2,2- difluoroethoxy)propoxy)phenyl]pyrimidine was prepared essentially as described in Example 8 using 5-benzyloxy-2-(4-hydroxy)phenyl]pyrimidine (0.97 g, 3.47 mmol) in place of 5-hexyl-2-(4-hydroxyphenyl)pyrimidine. The benzyl protecting group was removed by hydrogenation using 10% Pd on carbon in tetrahydrofuran under 3100 torr (60 psi) hydrogen pressure until the reaction was shown to be complete by thin layer chromatography. The Pd catalyst was removed by filtration, and the solvent was removed under reduced pressure to give 5-hydroxy-2-(4-((R)-2-fluoro-3-(2-(2-(nonafluorobutoxy)tetrafluoroethoxy)-2,2-difluoroethoxy)propoxy)phenyl]pyrimidine as a white solid. This hydroxyphenylpyrimidine (760 mg, 1.12 mmol), (R)-2-fluoro-decyl-p-toluenesulfonate (370 mg, 1.12 mmol), and potassium carbonate (150 mg, 1.12 mmol) in acetonitrile (30 ml) were stirred at reflux temperature until the reaction was shown to be complete by gas chromatography. The resulting product was then coated onto silica gel (2 g) and was purified by column chromatography (eluting with 15:1 hexane/ethyl acetate) to give 695 mg of the title compound as a white solid. The solid was further purified by recrystallization from methanol.

Example 19

Preparation of 5-((S)-2-Fluorodecyloxy)-2-[4-((R)-2-fluoro-3-(2-(2-(nonafluorobutoxy)tetrafluoroethoxy)-2,2,-difluoroethoxy)propoxy)phenyl]pyrimidine The title compound was prepared essentially as described in Example 18 using (S)-2-fluoro-decyl-p-toluenesulfonate (0.146 g, 0.44 mol) in place of (R)-2-fluoro-decyl-p-toluenesulfonate.

Example 20

Preparation of N-(4-Octyloxy)phenyl-(S)-5-((2-(2-(nonafluorobutoxy)tetrafluoroethoxy)-2,2-difluoroethoxy)methyl-2-oxazolidinone A one liter flask, equipped with a dropping addition funnel, a mechanical stirrer, a thermometer, and a reflux condenser was charged with (R)-epichlorohydrin (5 g, 0.54 mol) under positive nitrogen pressure and was heated to 75° C. A mixture of 2-(2-(nonafluorobutoxy)tetrafluoroethoxy) 2,2-difluoroethanol (22.8 g, 53 mmol) and potassium-t-butoxide (53 mL of 1M in t-butanol) was added to the flask over a period of 1.5 hours, with stirring. The flask was then cooled to ambient temperature and the contents distilled to yield (S)-2-(2-(nonafluorobutoxy)tetrafluoroethoxy)-2,2-difluoroethyl-glycidyl ether (8.8 g, b.p. 65° C. at 0.3 torr).

A solution of N-(4-benzyloxy)phenylethyl urethane (1.0 g, 3.68 mmol, prepared essentially as described by Iwakura et al. in J. Org. Chem. 29, 379 (1964)), (S)-2-(2-(nonafluorobutoxy)tetrafluoroethoxy)-2,2-difluoroethyl-glycidyl ether (1.8 g, 3.68 mmol), and triethyl amine (370 mg, 3.68 mmol) in tetrahydrofuran (5 ml) was heated to reflux temperature for 48 hours. The resulting product was coated onto silica gel and was purified by column chromatography (eluting with 20:1 toluene/ethyl acetate) to give 1.6 of a tan solid. The solid was dissolved in tetrahydrofuran (10 ml), and the resulting solution was stirred for 24 hours in the presence of 10% Pd on carbon (100 mg) under 3100 torr (60 psi) of hydrogen. The Pd catalyst was removed by filtration, and the filtrate was concentrated under reduced pressure to give 1.25 g of N-(4-hydroxy)phenyl-(S)-5-(2-(2-(nonafluorobutoxy)tetrafluoroethoxy)-2,2-difluoroethoxy) methyl-2-oxazolidinone as a white solid.

A solution of of this oxazolidinone (250 mg, 0.4 mmol), 1-bromooctane (116 mg, 0.6 mmol), and potassium carbonate (83 mg, 0.6 mmol) in acetonitrile (20 ml) was stirred at reflux temperature for 18 hours. The resulting product was coated on to silica gel (2 g) and was purified by column chromatography to give 370 mg of the title compound. The compound was further purified by recrystallization from methanol.

Example 21

Preparation of N-(4-Octyloxybenzoyl)phenyl-(S)-5-(2-(2-(nonafluorobutoxy)tetrafluoroethoxy)2,2-difluoroethoxy)methyl -2-oxazolidinone Triethylamine (230 mg, 1.76 mmol) was added to a solution of N-(4-hydroxy)phenyl-(S)-5-(2-(2-(nonafluorobutoxy)tetrafluoroethoxy)2,2-difluoroethoxy) methyl-2-oxazolidinone (500 mg, 0.88 mmol) and 4-octyloxybenzoyl chloride (220 mg, 0.88 mmol) in dichloromethane (10 ml). The resulting mixture was stirred at ambient temperature for 4 hours and was then coated onto silica gel and the resulting product purified by column chromatography. The product was further purified by recrystallization from methanol to give 533 mg of the product as a white solid.

Example 22

Preparation of 5-Octyl-2-[(4-(S)-5-oxymethyl-3-(2-(2-(nonafluorobutoxy)tetrafluoroethoxy)-2,2,-difluoroethoxy)-2(3H)furanone)phenyl]pyrimidine A one liter flask was fitted with an addition funnel, a mechanical stirrer, a reflux condenser, and a thermometer and was charged with 1,3-dibromopropane (360 g, 1.78 mol), 2-(2-(nonafluorobutoxy)tetrafluoroethoxy)2,2-difluoroethanol (150 g, 0.347 mol), and Adogen 464™ quaternary ammonium phase transfer catalyst (available from Aldrich Chemical, 30 g). The resulting mixture was heated to 70° C., and the mixture was maintained at 70°–90° C. while potassium hydroxide (84 g, 1.5 mol, dissolved in 50 mL water) was added dropwise with stirring. After complete addition, the mixture was maintained at 70°–80° C. for one hour, was cooled, and then water (300 mL) was added. The resulting upper aqueous layer of the mixture was discarded, and perfluorohexane was added to the remainder. Excess dibromopropane was decanted from the resulting mixture, and the remaining volatile components of the mixture were removed under reduced pressure. The resulting product, 3-(2-(2-(nonafluorobutoxy)tetrafluoroethoxy)-2,2-difluoroethoxy)-1-bromopropane, was purified by distillation on a six-plate Snyder column (b.p. 48°–52° C. at 0.05 torr).

A flask was then charged with dry dimethyl formamide and sodium hydride (1.3 g, 43.3 mmol, 80 weight percent dispersion in oil) under positive nitrogen pressure, followed by dropwise addition of diethyl malonate (7.1 g, 44 mmol) with stirring. When gas evolution ceased, $C_4F_9OC_2F_4OCF_2CH_2OC_3H_6Br$ (25 g, 40.6 mmol) was added to the flask, and the resulting mixture was heated to 85° C. and then stirred at ambient temperature overnight. The resulting lower fluorochemical phase of the mixture was separated, and the upper phase was treated with ether (60 mL) and water (40 mL) and then washed with brine. The resulting ether phase was added to the fluorochemical phase. The volatile components of this combined fluorochemical phase were removed under reduced pressure at 40° C., and then the product, $C_4F_9OC_2F_4OCF_2CH_2OC_3H_6CH(CO_2C_2H_5)_2$, was purified by distillation (b.p. 86°–90° C. at 0.05 torr).

A flask was then charged with the malonate product (4 g, 6.3 mmol), 5-octyl-2-((4-oxymethyl-(S)-2-oxiranyl)phenyl) pyrimidine (2.2 g, 6.8 mmol), potassium-t-butoxide (6.8 mL of 1M), and t-butanol (15 mL) and was then heated at 83°–87° C. for 4 hours with stirring. The resulting mixture was acidified with 4.5% aqueous HCl and was stirred at 0° C. for 30 minutes. The resulting yellow, gummy solid product was removed by filtration and was air-dried. The product was further purified by recrystallization from methanol. The cis(S,S) isomer of the product was isolated as a 4.9:1 ratio of the cis to trans, and the trans(S,R) isomer was isolated as a 7.3:1 ratio of the trans to cis isomers by liquid chromatography on silica gel using 4:1 hexanes/ethyl acetate as the eluent.

Examples 23 and 24

Preparation of 5-Octyl-2-[4-((S)-2-hydroxy-3-(4-(2-(2-(nonafluorobutoxy)tetrafluoroethoxy)2,2-difluoroethoxy)phenyl)propoxy)phenyl]pyrimidine and 5-Octyl-2-[4-((R)-2-fluoro-3-(4-(2-(2-(nonafluorobutoxy)tetrafluoroethoxy)2,2-difluoroethoxy)phenyl)propoxy)phenyl]pyrimidine Example 23 was prepared essentially as described in Examples 3 and 4 by combination of 4-(2-(2-(nonafluorobutoxy)tetrafluoroethoxy)-2,2-difluoroethoxy)phenol (1.4 g, 2.9 mmol, prepared essentially as described in U.S. Pat. No. 5,262,082 (Janulis et al.)) with (S)-5-octyl-2-[4-(2,3-oxiranylpropoxy)phenyl]pyrimidine (1.0 g, 2.9 mmol) to produce 5-octyl-2-[4-((S)-2-hydroxy-3-(4-(2-(2-(nonafluorobutoxy)tetrafluoroethoxy)2,2-difluoroethoxy)phenyl)propoxy)phenyl]pyrimidine (Example 23). This chiral (S)-hydroxy compound (1.5 g, 1.7 mmol) was treated with diethylaminosulfur trifluoride (0.6 g, 3.5 mmol) to produce Example 24.

Examples 25 and 26

Preparation of 5-Octyl-2-[4-((S)-2-hydroxy-3-(6-(2-(nonafluorobutoxy)tetrafluoroethoxy)-2,2,3,3,4,4,5,5,6,6-decafluorohexylyloxy)propoxy)phenyl]pyrimidine and 5-Octyl-2-[4-((R)-2-fluoro-3-(6-(2-(nonafluorobutoxy)tetrafluoroethoxy)-2,2,3,3,4,4,5,5,6,6-decafluorohexylyloxy)propoxy)phenyl]pyrimidine The title compounds were prepared essentially as described in Examples 3 and 4 by combining 6-(2-(nonafluorobutoxy)tetrafluoroethoxy)-2,2,3,3,4,4,5,5,6,6-decafluoro-1-hexanol (22.2 g, 35 mmol) with (S)-5-octyl-2-[4-(2,3-5 oxiranylpropoxy)phenyl]pyrimidine (10.0 g, 29.4 mmol) to produce 5-octyl-2-[4-((S)-2-hydroxy-3-(6-(2-(nonafluorobutoxy)tetrafluoroethoxy)-2,2,3,3,4,4,5,5,6,6-decafluorohexyloxy)propoxy)phenyl]pyrimidine (Example 25). This chiral (S)-hydroxy compound (20 g, 21 mmol) was treated with diethylaminosulfur trifluoride (6.6 g, 41 mmol) to produce Example 26. The structures of the compounds are shown in Table 1.

Examples 27 and 28

Preparation of 5-Octyl-2-[4-((S)-2-hydroxy-3-(4-(2-(nonafluorobutoxy)tetrafluoroethoxy)-2,2,3,3,4,4-hexafluorobutyloxy)propoxy)phenyl]pyrimidine and 5-Octyl-2-[4-((R)-2-fluoro-3-(4-(2-(nonafluorobutoxy)tetrafluoroethoxy)-2,2,3,3,4,4-hexafluorobutyloxy)propoxy)phenyl]pyrimidine The title compounds were prepared essentially as described in Examples 3 and 4 by combining 4-(2-(nonafluorobutoxy)tetrafluoroethoxy)-2,2,3,3,4,4-hexafluoro-1-butanol (3.7 g, 7 mmol) with (S)-5-octyl-2-[4-(2,3-oxiranylpropoxy)phenyl]pyrimidine (2.0 g, 5.87 mmol) to produce 5-octyl-2-[4-((S)-2-hydroxy-3-(4-(2-(nonafluorobutoxy)tetrafluoroethoxy)-2,2,3,3,4,4-hexafluorobutyloxy)propoxy)phenyl]pyrimidine (Example 27). This chiral (S)-hydroxy compound (3 g, 3.4 mmol) was treated with diethylaminosulfur trifluoride (1.1 g, 6.8 mmol) to produce Example 28. The structures of the compounds are shown in Table 1.

Examples 29 and 30

Preparation of 5-Octyl-2-[6-((S)-2-hydroxy-3-(6-(2-(2-(nonafluorobutoxy)tetrafluoroethoxy)tetrafluoroethoxy)-2,2,3,3,4,4,5,5,6,6-decafluorohexyloxy)propoxy)phenyl]pyrimidine and 5-Octyl-2-[6-((R)-2-fluoro-3-(6-(2-(2-(nonafluorobutoxy)tetrafluoroethoxy)tetrafluoroethoxy)-2,2,3,3,4,4,5,5,6,6-decafluorohexyloxy)propoxy)phenyl]pyrimidine The title compounds were prepared essentially as described in Examples 3 and 4 by combining 6-(2-(2-(nonafluorobutoxy)tetrafluoroethoxy)tetrafluoroethoxy-2,2,3,3,4,4,5,5,6,6-decafluoro-1-hexanol (11.5 g, 15.4 mmol) with (S)-5-octyl-2-[4-(2,3-oxiranylpropoxy)phenyl]pyrimidine (5.0 g, 15.34 mmol) to produce 5-octyl-2-[4-((S)-2-hydroxy-3-(6-(2-(2-(nonafluorobutoxy)tetrafluoroethoxy)tetrafluoroethoxy)-2,2,3,3,4,4,5,5,6,6-decafluorohexyloxy)propoxy)phenyl]pyrimidine (Example 29). This chiral (S)-hydroxy compound (10.0 g, 9.2 mmol) was treated with diethylaminosulfur trifluoride (5.8 g, 36 mmol) to produce Example 30. The structures of the compounds are shown in Table 1.

Examples 31 and 32

Preparation of 5-Octyl-2-[4-((S)-2-hydroxy-3-(2,2,2-trifluoroethoxy)propoxy)phenyl]pyrimidine and 5-Octyl-2-[4-((R)-2-fluoro-3-(2,2,2-trifluoroethoxy)propoxy)phenyl]pyrimidine The title compounds were prepared essentially as described in Examples 3 and 4 by combining 2,2,2-trifluoroethanol (1.1 g, 11.2 mmol) with (S)-5-octyl-2-[4-(2,3-oxiranylpropoxy)phenyl]pyrimidine (2.0 g, 5.6 mmol) to produce 5-octyl-2-[4-((S)-2-hydroxy-3-(2,2,2-trifluoroethoxy)propoxy)phenyl]pyrimidine (Example 31). This chiral (S)-hydroxy compound (2.0 g, 4.5 mmol) was treated with diethylaminosulfur trifluoride (1.46 g, 9.0 mmol) to produce Example 32. The structures of the compounds are shown in Table 1.

Example 33

Preparation of (S)-5-Octyl-2-[4-(2-(2-(nonafluorobutoxy)tetrafluoroethoxy)-2,2-difluoroethoxy)methyl-2-oxazolidinone)phenyl]pyrimidine 5-Octyl-2-(4-aminophenyl)pyrimidine was prepared by the following modification of the procedure described by Zaschke et al. in Z. Chem. 15, 441 (1975). Sodium methoxide (25% in methanol, 79.7 g, 3.07 eq) was added to a solution of 4-amino benzamidine hydrochloride (25 g) and 2-octyl-3-dimethylamino acrolein (25.7 g, 1.0 eq) in methanol (400 ml). The resulting mixture was heated to reflux temperature for 18 hours and was then cooled to ambient temperature. The mixture was acidified with concentrated HCl and was then filtered. The filtrate was diluted with 400 ml of water and was extracted with three 200 ml aliquots of toluene. The combined extracts were concentrated, dissolved in 400 ml of methanol, filtered, and made strongly acidic by saturation with gaseous HCl. Removal of the solvent provided a red oil which was treated with 250 ml of hot acetone and allowed to cool. Filtration gave 7.5 g of the crude HCl salt. The salt (1 g) was neutralized with 5 equivalents of triethylamine in tetrahydrofuran (10 ml), and the resulting free amine was purified by liquid chromatography on silica gel using 20:1 dichloromethane/ethyl acetate as the eluent.

A solution of the free amine (5-octyl-2-(4-aminophenyl) pyrimidine, 0.37 g, 1.31 mmol) in acetonitrile (2 ml) was added dropwise to a solution of magnesium perchlorate (0.29 g, 1.31 mmol) and 2-(2-(nonafluorobutoxy) tetrafluoroethoxy)ethyl-glycidyl ether (0.64 g, 1.31 mmol) in acetonitrile (1 ml). The resulting mixture was stirred under a nitrogen atmosphere for 18 hours, during which time a white precipitate formed. The precipitate was isolated by filtration to give 0.88 g of crude amino alcohol (5-octyl-2-(4-(3-(2-(2-(nonafluorobutoxy)tetrafluoroethoxy)-2,2-difluoroethoxy-2-hydroxypropyl)aminophenyl)pyrimidine). A solution of triphosgene (96 mg, 0.33 mmol) in dichloromethane (2 ml) was then added dropwise to a 0° C. solution of the amino alcohol (500 mg, 0.56 mmol) and pyridine (0.26 ml, 3.25 mmol) in dichloromethane (4 ml). The resulting mixture was stirred for 1 hour at 0° C. and then for 3 hours at ambient temperature. The mixture was then coated onto silica gel and purified by chromatography on silica gel using 15:1 dichloromethane/ethyl acetate as the eluent. The resulting product was further purified by recrystallization from hexane.

Example 34

Preparation of 5-Octyl-2-[4-((S)-2-hydroxy-3-(8-(2-(nonafluorobutoxy)tetrafluoroethoxy)-2,2,3,3,4,4,5,5,6,6,7,7,8,8-tetradecafluorooctyloxy)propoxy) phenyl]pyrimidine The title compound was prepared essentially as described in Examples 3 and 4 by combining 8-(2-(nonafluorobutoxy) tetrafluoroethoxy)-2,2,3,3,4,4,5,5,6,6,7,7,8,8-tetradecafluoro-1-octanol (6.4 g, 8.8 mmol) with (S)-5-octyl-2-[4-(2,3-oxiranylpropoxy)phenyl]pyrimidine (2.5 g, 7.35 mmol).

Example 35

Preparation of 5-Octyl-2-[4-((S)-2-hydroxy-3-(4-(2-(tridecafluorohexyloxy)tetrafluoroethoxy)-2,2,3,3,4,4-hexafluorobutyloxy)propoxy)phenyl]pyrimidine The title compound was prepared essentially as described in Examples 3 and 4 by combining 4-(2-(tridecafluorohexyloxy)tetrafluoroethoxy)-2,2,3,3,4,4-hexafluorobutanol (6.4 g, 10.1 mmol) with (S)-5-octyl-2-[4-(2,3-oxiranylpropoxy)phenyl]pyrimidine (4.0 g, 11.8 mmol).

Comparative Example 1

Preparation of 5-Octyl-2-[4-((R)-2-fluoro-3-(2-(2-butoxyethoxy)ethoxy)propoxy)phenyl]pyrimidine Boron trifluoride etherate (1.3 ml, 10.8 mmol) was added dropwise to a 0° C. solution of 2-(2-butoxyethoxy)ethanol (35 g, 216 mmol) and (S)-epichlorohydrin (10 g, 108 mmol). The resulting mixture was warmed slowly to ambient temperature and was stirred for 18 hours at ambient temperature. 1-chloro-3-(2-(2-butoxyethoxy)ethoxy)-2-propanol was distilled from the mixture (105°–110° C. at 0.3 torr).

Potassium carbonate (2.1 g, 15.7 mmol) was added to a solution of 5-octyl-2-(4-hydroxyphenyl)pyrimidine (3.0 g, 10.5 mmol) and 1-chloro-3-(2-(2-butoxyethoxy)ethoxy)-2-propanol (2.7 g, 10.5 mmol) in N,N-dimethylformamide (100 ml). The resulting mixture was stirred at reflux temperature for 18 hours and then cooled to ambient temperature. The mixture was diluted with water (100 ml) and was extracted with three 100 ml aliquots of diethyl ether. The extracts were dried (over $MgSO_4$), filtered, and concentrated to give crude product as an oil. 5-Octyl-2-[4-((S)-2-hydroxy-3-(2-(2-(butoxy)ethoxy)ethoxy)propoxy)phenyl] pyrimidine was then isolated by chromatography. The chiral (S)-hydroxy compound (3.5 g, 7.5 mmol) was treated with diethylaminosulfur trifluoride (5.3 g, 15 mmol) to produce Comparative Example 1.

TABLE 1

| Example No. | Structure |
| --- | --- |
| 1 | $C_8H_{17}$—pyrimidine—phenyl—O—CHF—$CH_2C_6F_{13}$ |
| 2 | $C_8H_{17}$—pyrimidine—phenyl—O—CHF—$OCH_2C_5F_{11}$ |
| 3 | $C_8H_{17}$—pyrimidine—phenyl—O—CH(OH)—$OCH_2CF_2OC_2F_4OC_4F_9$ |

TABLE 1-continued
| Example No. | Structure |
|---|---|
| 4 | 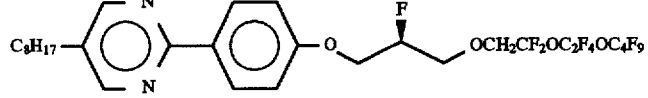 |
| 5 | 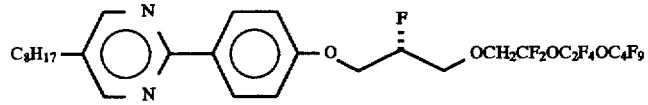 |
| 6 | 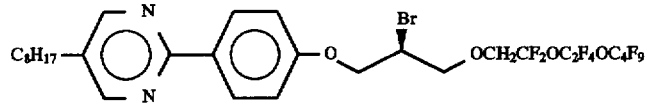 |
| 7 | 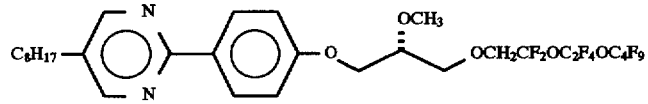 |
| 8 | 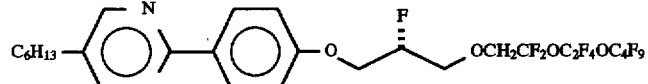 |
| 9 | 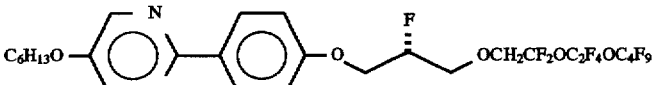 |
| 10 | 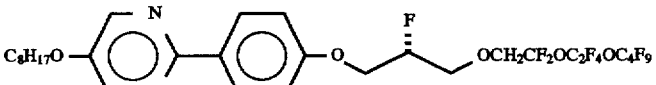 |
| 11 | 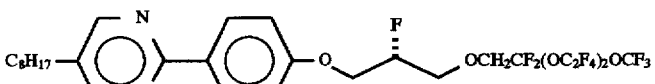 |
| 12 | 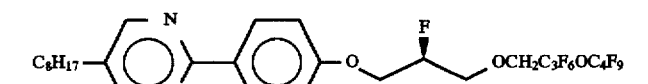 |
| 13 | 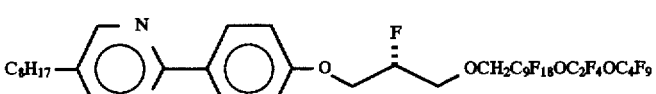 |
| 14 | 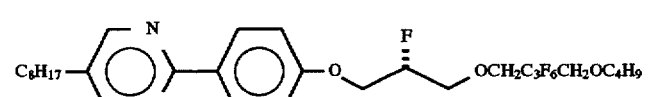 |
| 15 | 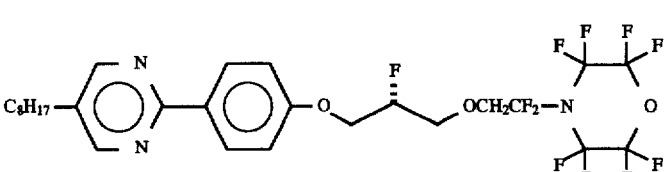 |

TABLE 1-continued

| Example No. | Structure |
|---|---|
| 16 | C₈H₁₇–[pyrimidine]–[phenyl]–O–CH₂CHF–CH₂–OC₂H₄OCH₂CF₂OC₂F₄OC₄F₉ |
| 17 | C₈H₁₇–[2,3-difluorobiphenyl]–O–CH₂CHF–CH₂–OCH₂CF₂OC₂F₄OC₄F₉ |
| 18 | C₆H₁₃–CHF–CH₂–O–[pyrazine]–[phenyl]–O–CH₂CHF–CH₂–OCH₂CF₂OC₂F₄OC₄F₉ |
| 19 | C₆H₁₃–CHF–CH₂–O–[pyrazine]–[phenyl]–O–CH₂CHF–CH₂–OCH₂CF₂OC₂F₄OC₄F₉ |
| 20 | C₈H₁₇O–[phenyl]–[oxazolidinone]–CH₂–OCH₂CF₂OC₂F₄OC₄F₉ |
| 21 | C₈H₁₇O–[phenyl]–C(=O)–O–[phenyl]–[oxazolidinone]–CH₂–OCH₂CF₂OC₂F₄OC₄F₉ |
| 22 | C₈H₁₇–[pyrimidine]–[phenyl]–O–CH₂–[γ-butyrolactone]–(CH₂)₃OCH₂CF₂OC₂F₄OC₄F₉ |
| 22 CIS | C₈H₁₇–[pyrimidine]–[phenyl]–O–CH₂–[γ-butyrolactone]–(CH₂)₃OCH₂CF₂OC₂F₄OC₄F₉ |
| 22 TRANS | C₈H₁₇–[pyrimidine]–[phenyl]–O–CH₂–[γ-butyrolactone]–(CH₂)₃OCH₂CF₂OC₂F₄OC₄F₉ |
| 23 | C₈H₁₇–[pyrimidine]–[phenyl]–O–CH₂–CH(OH)–CH₂–O–[phenyl]–OCH₂CF₂OC₂F₄OC₄F₉ |
| 24 | C₈H₁₇–[pyrimidine]–[phenyl]–O–CH₂–CHF–CH₂–O–[phenyl]–OCH₂CF₂OC₂F₄OC₄F₉ |

TABLE 1-continued

| Example No. | Structure |
|---|---|
| 25 | $C_8H_{17}$-[pyrimidine]-[phenyl]-O-CH$_2$-CH(OH)-CH$_2$-OCH$_2$C$_6$F$_{10}$OC$_2$F$_4$OC$_4$F$_9$ |
| 26 | $C_8H_{17}$-[pyrimidine]-[phenyl]-O-CH$_2$-CHF-CH$_2$-OCH$_2$C$_6$F$_{10}$OC$_2$F$_4$OC$_4$F$_9$ |
| 27 | $C_8H_{17}$-[pyrimidine]-[phenyl]-O-CH$_2$-CH(OH)-CH$_2$-OCH$_2$C$_3$F$_6$OC$_2$F$_4$OC$_4$F$_9$ |
| 28 | $C_8H_{17}$-[pyrimidine]-[phenyl]-O-CH$_2$-CHF-CH$_2$-OCH$_2$C$_3$F$_6$OC$_2$F$_4$OC$_4$F$_9$ |
| 29 | $C_8H_{17}$-[pyrimidine]-[phenyl]-O-CH$_2$-CH(OH)-CH$_2$-OCH$_2$C$_5$F$_{10}$O(C$_2$F$_4$O)$_2$C$_4$F$_9$ |
| 30 | $C_8H_{17}$-[pyrimidine]-[phenyl]-O-CH$_2$-CHF-CH$_2$-OCH$_2$C$_5$F$_{10}$O(C$_2$F$_4$O)$_2$C$_4$F$_9$ |
| 31 | $C_8H_{17}$-[pyrimidine]-[phenyl]-O-CH$_2$-CH(OH)-CH$_2$-OCH$_2$CF$_3$ |
| 32 | $C_8H_{17}$-[pyrimidine]-[phenyl]-O-CH$_2$-CHF-CH$_2$-OCH$_2$CF$_3$ |
| 33 | $C_8H_{17}$-[pyrimidine]-[phenyl]-N(COCH$_3$)-CH$_2$-CH(O-)-CH$_2$-OCH$_2$CF$_2$OC$_2$F$_4$OC$_4$F$_9$ |
| 34 | $C_8H_{17}$-[pyrimidine]-[phenyl]-O-CH$_2$-CH(OH)-CH$_2$-OCH$_2$C$_7$F$_{14}$OC$_2$F$_4$OC$_4$F$_9$ |
| 35 | $C_8H_{17}$-[pyrimidine]-[phenyl]-O-CH$_2$-CH(OH)-CH$_2$-OCH$_2$C$_3$F$_6$OC$_2$F$_4$OC$_6$F$_{13}$ |
| Comparative Example 1 | $C_8H_{17}$-[pyrimidine]-[phenyl]-O-CH$_2$-CHF-CH$_2$-OCH$_2$CH$_2$OC$_2$H$_4$OC$_4$H$_9$ |

The compounds of Table 1 were evaluated for transition temperatures by differential scanning calorimetry (DSC) and/or optical observation of material phase changes using a Linkham TMH600 hot stage and a polarizing microscope. The transition temperatures (°C.) were obtained upon cooling through the isotropic state (I) to the smectic A mesophase ($S_A$), the smectic C. mesophase ($S_C$), and higher order mesophases (M1 and M2) and are set forth in Table 2 below.

TABLE 2

| Example No. | I to $S_A$ | to $S_C$ | to $S_{M1}$ | to $S_{M2}$/K | $S_M$ to $S_C$, $S_A$, or I |
|---|---|---|---|---|---|
| 1 | 128.9 | — | — | 90.8 | 103 |
| 2 | 84.4 | — | — | 69.5 | 90.2 |
| 3 | 73.5 | 70.5 | — | 24.2 | 52.9 |
| 4 | 93 | 64.2 | — | −10.4 | 40.1 |
| 5 | 93 | 64.21 | — | −12.1 | 39.9 |
| 6 | 49.9 | 48.7 | — | 45.8 | 51 |
| 7 | 73.7 | — | — | −31.8 | 9.7 |
| 8 | 90.7 | 49.3 | — | 20.9 | 39.7 |
| 9 | 121.1 | 98.0 | — | 24.0 | 44.6 |
| 10 | 117.4 | 101.8 | — | 6.1 | 46.3 |
| 11 | 89.7 | 57.1 | — | −12.7 | 33.3 |
| 12 | 94 | 65.9 | — | 3.5 | 44.1 |
| 13 | 136 | 105 | — | 69.9 | 82.8 |
| 14 | — | — | — | — | 69.6 |
| 15 | 53.0 | — | — | −19.2 | 34.1 |
| 16 | 76.0 | — | — | −25 | −9.6 |
| 17 | 28.2 | — | — | −19.4 | −1.45 |
| 18 | 106.7 | 89.7 | — | 63.23 | 65.9 |
| 19 | 102.7 | 83.7 | 59.5 | 48.6 | 67.5 |
| 20 | 45.1 | — | — | 32.1 | 53.9 |
| 21 | 152.7 | — | — | 69.6 | 83.3 |
| 22 | 99.1 | 57.3 | — | <−14 | >21 |
| 22 cis | 95.8 | — | — | 58.6 | 79.3 |
| 22 trans | 98.8 | — | — | 42.6 | 70.4 |
| 24 | 83.7 | — | — | 72.4 | 90.9 |
| 26 | 113.5 | 86.9 | — | 23.5 | 39.9 |
| 28 | 99.5 | 68.6 | 32.6 | −1.4 | 36.1 |
| 30 | 115.9 | 86.3 | — | 25.0 | 43.0 |
| 32 | — | — | — | — | mp = 88–89° C. |
| 33 | 140 | — | — | 128 | 138 |
| Comparative 1 | — | — | — | <20° C. | — |

The data in Table 2 shows that most of the compounds of the invention exhibit smectic mesophases and that many of the compounds exhibit a broad smectic C. mesophase, which makes the compounds well-suited for use in liquid crystal display devices. As a result of the breadth of the smectic C. mesophase, the compounds are useful in admixture with themselves or with other liquid crystal compounds, even at high concentration. In contrast with Example 5 which shows a broad smectic C. mesophase, Comparative Example 1 shows no liquid crystal behavior above 20° C.

Examples 36–53 describe liquid crystal compound mixtures and/or liquid crystal display devices of the invention.

Example 36

A device containing a chiral compound of this invention (Example 5) was prepared essentially as described in U.S. Pat. No. 5,377,033 (Radcliffe) and filled with a mixture of 9.7 weight percent 5-octyl-2-[4-((R)-2-fluoro-3-(2-(2-(nonafluorobutoxy)tetrafluoroethoxy)-2,2,-difluoroethoxy)propoxy)phenyl]pyrimidine (Example 5), 11.5 weight percent 5-octyloxy-2-[4-(2-(2-(nonafluorobutoxy)tetrafluoroethoxy)-2,2-difluoroethoxy)phenyl]pyrimidine (prepared essentially as described in U.S. Pat. No. 5,262,082 (Janulis et al.)), 11.6 weight percent 5-decyloxy-2-[4-(4-(nonafluorobutoxy)octafluorobutoxy)-2,2,3,3,4,4-hexafluorobutoxy)phenyl]pyrimidine, 12.6 weight percent 5-decyloxy-2-[2-(2-(tridecafluorohexyloxy)tetrafluoroethoxy)-2,2-difluoroethoxy)phenyl]pyrimidine, 6.6 weight percent 5-octyl-2-[4-(3-(4-(2-(2-(nonafluorobutoxy)tetrafluoroethoxy)2,2-difluoroethoxy)phenyl)phenyl]pyrimidine, 13.4 weight percent 5-octyl-2-[4-(4-(nonafluorobutoxy)octafluorobutoxy)-2,2,3,3,4,4-hexafluorobutoxy)phenyl]pyrimidine, and 34.7 weight percent 5-decyl-2-[4-(4-(nonafluorobutoxy)octafluorobutoxy)-2,2,3,3,4,4-hexafluorobutoxy)phenyl]pyrimidine.

The ITO-constituted electrodes of the device were connected to an arbitrary waveform generator with variable output voltage. The device was driven by a voltage waveform consisting of bipolar, square pulses of ±10V/μm amplitude, spaced 30 milliseconds apart by a train of square pulses having the same width and 3.3 V/μm amplitude. The device was heated to the temperatures noted in Table 3 (below) and the polarization (nC/cm$^2$), the $\tau_{electric}$, the smectic viscosity, and the tilt angle $\phi_t$ were determined as described below:

The polarization of the device was determined essentially as described by Miyasato et al. in Jap. J. Appl. Phys. 22, 661 (1983). The electronic response time, $\tau_{electric}$, was derived from the displacement current of the ferroelectric liquid crystal device under an applied square voltage pulse. The current was viewed on a 100 megahertz bandwidth oscilloscope. The usual decaying exponential, associated with a dielectric filled capacitor, was followed by the spontaneous polarization ($P_s$) switching pulse. The time from the rising edge of the voltage pulse to the peak of the $P_s$ pulse was taken to be $\tau_{electric}$. The rotational viscosity (smectic viscosity, η) was calculated as shown below:

$$\eta(10^{-3}\ kg/m\cdot s) = 0.01 \cdot P_s \cdot E \cdot \tau_{electric}$$

where the units of $P_s$, E, and $\tau_{electric}$ are respectively nC/cm$^2$, V/μm, and μs. The tilt angle $\phi_t$ of the mixture was taken to be half the angle separating the extinction points of the driven states. The results given in Table 3 show fast response times over a wide temperature range.

In addition, the phase transition temperatures of the mixture were measured essentially as described above and were found to be: I to A=105.8° C., A to C=72.7° C., and C to M=−9.0° C. The phase transition temperatures of the achiral base material (i.e., the above-described mixture without the chiral dopant) were also measured and were found to be: I to A=106.2° C., A to C=70.5° C., and C to M=−5.6° C. Thus, the smectic C. temperature range of the mixture was essentially the same as that of the achiral base.

Comparative Example 2

A mixture was prepared essentially as described in Example 36 using the same achiral base mixture and 9.7 weight percent 5-octyl-2-[4-((R)-2-fluoro-3-(2-(2butoxyethoxy)ethoxy)propoxy)phenyl]pyrimidine as chiral dopant (instead of Example 5). The phase transition temperatures of the resulting mixture were found to be: I to A=99.5° C., A to C=31.6° C., and C to M=22.8° C. This data shows a severe loss of the smectic C. mesophase range relative to Example 36, which loss effectively prevents the use of this comparative mixture in liquid crystal display devices.

Examples 37–52

Other devices were constructed using commercially available polyimides (such as RN-305, RN-741, or RN-763 available from Nissan Chemical Industries, Japan) in place of nylon 6/6, or using commercially available cells (such as a DisplayTech cell, available from DisplayTech in Boulder, Colo., or an EHC cell, available from EHC Ltd., Japan). Since the properties measured to characterize the present invention are largely independent of cell type, a variety of cells could be utilized. Polarization, viscosity, response time, and tilt angle are effectively independent of the alignment system in a cell, although there are minor differences in some properties (such as better alignment in nylon cells).

Example 37

A device was prepared and evaluated essentially as described in Example 36 using a mixture of 5 weight percent 5-octyl-2-[(4-(S)-5-oxymethyl-3-(2-(2-(nonafluorobutoxy) tetrafluoroethoxy)-2,2,-difluoroethoxy)-2(3H)furanone) phenyl]pyrimidine (Example 22) as the chiral dopant, 63.3 weight percent 5-octyl-2-[4-(6-(2-(nonafluorobutoxy) tetrafluoroethoxy)-2,2,3,3,4,4,5,5,6,6-decafluorohexyloxy) phenyl]pyrimidine, and 31.6 weight percent 5-octyl-2-[4-(2-(2-(nonafluorobutoxy)tetrafluoroethoxy)-2,2-difluoroethoxy)phenyl]pyrimidine. The results are shown in Table 3 below.

In addition, the phase transition temperatures of the mixture were measured essentially as described above and were found to be: I to A=99.7° C., A to C=54.1° C., and C to K=−16.1° C.

Comparative Example 3

Into a flask fitted with a stirrer, a thermometer, and a reflux condenser was charged KOH (24.6 g, 373 mmol, dissolved in 25 mL water), 1,1-dihydroperfluoromethoxyethoxyethoxyethanol (50 g, 125.6 mmol; prepared by sodium borohydride reduction of the corresponding methyl ester, essentially as described in Example 3 of U.S. Pat. No. 5,262,082 (Janulis et al.)), tetrabutylammonium hydrogen sulfate (3.0 g, 8.8 mmol), and 1,6-dibromohexane (150 g). The resulting reaction mixture was heated at 100° C. for three hours, cooled to room temperature, and diluted with water (75 mL) and perfluoro-N-methyl morpholine (153 g) in a separatory funnel. The resulting lower fluorochemical phase was removed from the funnel, and the solvent was distilled at ambient pressure. The resulting residue was distilled, and the fraction boiling at 83°–97° C. at 0.3 torr was collected. GC/MS analysis of this fraction showed that it contained 12 area % dibromohexane, 71 area % desired 6-(1,1-dihydroperfluoro(methoxyethoxyethoxyethoxy))-1-bromohexane ($CF_3O(CF_2CF_2O)_2CF_2CH_2O(CH_2)_6Br$), and 7 area % $CF_3O(CF_2CF_2O)_2CF_2CH_2O(CH_2)_6OCH_2CF_2(OCF_2CF_2)_2OCF_3$.

Using essentially the procedure of Example 8, 5-hydroxy-2-(4-(dihydro-5-(R)-oxymethyl-3-(R)-hexyl-2(3H)-furanone)phenyl)pyrimidine (0.20 g, 0.54 mmol) was combined with potassium carbonate (0.09 g, 0.65 mmol) and 6-(1,1-dihydroperfluoro(methoxyethoxyethoxyethoxy))-1-bromohexane (0.30 g, 0.54 mmol) in acetonitrile (20 mL) to yield 0.18 g of product, a 90:10 mixture of cis/trans dihydrofuranone isomers (as determined by $^1H$ nuclear magnetic resonance spectroscopy).

A device was prepared and evaluated essentially as described in Example 36 using a mixture of 5 weight percent of the product (5-(6-(1,1-dihydroperfluoro(((2-methoxyethoxy)ethoxy)ethoxy)hexyloxy-2-(4-(dihydro-5-(R)-oxymethyl-3-(R)-hexyl-2-(3H)-furanone)phenyl) pyrimidine, prepared as described above), 63.3 weight percent 5-octyl-2-[4-(6-(2-(nonafluorobutoxy) tetrafluoroethoxy)-2,2,3,3,4,4,5,5,6,6-decafluorohexyloxy) phenyl]pyrimidine, and 31.6 weight percent 5-octyl-2-[4-(2-(2-(nonafluorobutoxy)tetrafluoroethoxy)-2,2-difluoroethoxy)phenyl]pyrimidine. The results shown in Table 3 indicate that Example 37 exhibits a much higher polarization than that of this Comparative Example at similar concentrations of chiral dopant. Thus, this data shows the importance of the position of the chiral moiety relative to the fluorochemical group.

In addition, the phase transition temperatures of the mixture were measured essentially as described above and were found to be: I to A=100.6° C., A to C=51.5° C., and C to K=<−10° C.

Example 38

A device was prepared and evaluated essentially as described in Example 36 using a mixture of 5 weight percent 5-octyl-2-[4-((R)-2-hydroxy-3-(2-(2-(nonafluorobutoxy) tetrafluoroethoxy)-2,2,-difluoroethoxy)propoxy)phenyl] pyrimidine (Example 3) as the chiral dopant, 63.3 weight percent 5-octyl-2-[4-(6-(2-(nonafluorobutoxy) tetrafluoroethoxy)-2,2,3,3,4,4,5,5,6,6-decafluorohexyloxy) phenyl]pyrimidine, and 31.6 weight percent 5-octyl-2-[4-(2-(2-(nonafluorobutoxy)tetrafluoroethoxy)-2,2-difluoroethoxy)phenyl]pyrimidine. The results given in Table 3 show a low viscosity for the mixture, which provides a fast response time in spite of the low polarization exhibited.

In addition, the phase transition temperatures of the mixture were measured essentially as described above and were found to be: I to A=101.1° C., A to C=54.5° C., and C to K=below room temperature.

Example 39

A device was prepared and evaluated essentially as described in Example 36 using a mixture of 20 weight percent 5-octyl-2-[4-((R)-2-hydroxy-3-(2-(2-(nonafluorobutoxy)tetrafluoroethoxy)-2,2,-difluoroethoxy) propoxy)phenyl]pyrimidine (Example 3) as the chiral dopant, 53.3 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine (prepared essentially by the methods described in U.S. Pat. No. 5,262,082 (Janulis et al.)), and 26.6 weight percent 5-octyl-2-[4-(2-(2-(nonafluorobutoxy)tetrafluoroethoxy)-2,2-difluoroethoxy) phenyl]pyrimidine. The results given in Table 3 show a low viscosity for the mixture, which provides a fast response time in spite of the low polarization exhibited.

In addition, the phase transition temperatures of the mixture were measured essentially as described above and were found to be: I to A=96.8° C., A to C=54.3° C., and C to K=below room temperature.

Example 40

A device was prepared and evaluated essentially as described in Example 36 using 100 weight percent 5-octyl-2-[4-((R)-2-fluoro-3-(2-(2-(nonafluorobutoxy) tetrafluoroethoxy)-2,2,-difluoroethoxy)propoxy)phenyl] pyrimidine (Example 5). The results given in Table 3 show very fast response times, high polarizations, and low viscosities. In addition, the response times are relatively temperature-independent.

Example 41

A device was prepared and evaluated essentially as described in Example 36 using a mixture of 50.1 weight percent 5-octyl-2-[(4-(S)-5-oxymethyl-3-(2-(2-(nonafluorobutoxy)tetrafluoroethoxy)-2,2,-difluoroethoxy)-2(3H)furanone)phenyl]pyrimidine (Example 22) as the chiral dopant, 33.3 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine (prepared essentially by the methods described in U.S. Pat. No. 5,262,082 (Janulis et al.)), and 16.6 weight percent 5-octyl-2-[4-(2-(2-(nonafluorobutoxy)tetrafluoroethoxy)-2,2-difluoroethoxy) phenyl]pyrimidine (prepared essentially as described in U.S. Pat. No. 5,262,082). The results given in Table 3 show very fast response times and high polarization.

In addition, the phase transition temperatures of the mixture were measured essentially as described above and were found to be: I to A=96.6° C., A to C=51.5° C., and C to K=21.4° C. The phase transition temperatures of the achiral base material (i.e., the above-described mixture without the chiral dopant) were also measured and were found to be: I to A=99.5° C., A to C=53.8° C., and C to K=<-10° C. Thus, the use of this chiral compound of the invention (Example 22) at high concentration in an achiral base mixture provides minimal suppression of the smectic C. mesophase.

Example 42

A device was prepared and evaluated essentially as described in Example 36 using a mixture of 10 weight percent 5-octyloxy-2-[4-((R)-2-fluoro-3-(2-(2-(nonafluorobutoxy)tetrafluoroethoxy)-2,2,-difluoroethoxy) propoxy)phenyl]pyrimidine (Example 10) as the chiral dopant, 63.3 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine, and 31.6 weight percent 5-octyl-2-[4-(2-(2-(nonafluorobutoxy) tetrafluoroethoxy)-2,2-difluoroethoxy)phenyl]pyrimidine. The results are shown in Table 3 below.

In addition, the phase transition temperatures of the mixture were measured essentially as described above and were found to be: I to A=106.5° C., A to C=60.5° C., and C to K=<-10° C.

Comparative Example 4

2-(S)-fluorooctanol (3.0 g, 20.2 mmol; which can be prepared by the procedure described by H. Nohira et al. in Mol. Cryst. Liq. Cryst. 180B, 379–88 (1990)) was combined with toluene sulfonyl chloride (4.0 g, 21.2 mmol), ethyl diisopropyl amine (5.2 g, 40.4 mmol), and dimethylaminopyridine (123 mg, 1.0 mmol) in methylene chloride (50 mL). The resulting mixture was stirred at room temperature overnight. The resulting crude tosylate product was purified by flash chromatography on silica gel, eluting with 10 parts by volume of hexane and 1 part by volume of ethyl acetate.

A three-necked flask equipped with a magnetic stir bar, a condenser, and a nitrogen inlet was charged with potassium carbonate (380 mg, 2.74 mmol) and acetonitrile (20 mL). With stirring, 5-hydroxy-2-(4-(1,1-dihydroperfluoro-2-(butoxyethoxy)ethoxy)phenyl)pyrimidine (1.5 g, 2.49 mmol; prepared essentially as in Example 18 above with substitution of $C_4F_9OC_2F_4OCF_2CH_2OSO_2CF_3$ (4.86 g, 8.6 mmol) for 3-(2-[2-(nonafluorobutoxy)tetrafluoroethoxy]-2,2-difluoroethoxy)-(R)-2-fluoropropyl-1-p-toluenesulfonate) was slowly added to the resulting mixture. The mixture was stirred at room temperature for 30 minutes. 1-p-toluenesulfonoxy-2-(S)-fluorooctane (0.75 g, 2.49 mmol) was then added to the stirred mixture. The mixture was heated to reflux overnight and then poured into a separatory funnel containing water (~20 mL). The resulting layers were separated, and the aqueous phase was extracted with diethyl ether and purified by chromatography (essentially as in Example 8 above), eluting with 10 parts by volume of hexane and 1 part by volume of ethyl acetate. The yield of desired product was 1.4 g. The structure of the product was confirmed by $^1H$ and $^{19}F$ nuclear magnetic resonance spectroscopy.

A device was prepared and evaluated essentially as described in Example 36 using a mixture of 10 weight percent of the product (5-((S)-2-fluorooctyloxy)-2-[4-(2-(2-(nonafluorobutoxy)tetrafluoroethoxy)-2,2-difluoroethoxy) phenyl]pyrimidine, prepared essentially as described above), 63.3 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine, and 31.6 weight percent 5-octyl-2-[4-(2-(2-(nonafluorobutoxy) tetrafluoroethoxy)-2,2-difluoroethoxy)phenyl]pyrimidine. The results shown in Table 3 indicate that Example 42 exhibits a much higher polarization than that of this Comparative Example (which effectively does not respond to an electric field) at similar concentrations of chiral dopant. Thus, this data shows the importance of the position of the chiral moiety relative to the fluorochemical group.

In addition, the phase transition temperatures of the mixture were measured essentially as described above and were found to be: I to A=101° C., A to C=56.5° C., and C to K=0.1° C.

Example 43

A device was prepared and evaluated essentially as described in Example 36 using 100 weight percent 5-octyl-2-[4-((S)-2-fluoro-3-(2-(2-(nonafluorobutoxy) tetrafluoroethoxy)-2,2,-difluoroethoxy)propoxy)phenyl] pyrimidine (Example 4). The results given in Table 3 show very fast response times, high polarizations, and low viscosities. In addition, the response times are relatively temperature-independent.

Example 44

A device was prepared and evaluated essentially as described in Example 36 using 100 weight percent 5-hexyl-2-[4-((R)-2-fluoro-3-(2-(2-(nonafluorobutoxy) tetrafluoroethoxy)-2,2,-difluoroethoxy)propoxy)phenyl] pyrimidine (Example 8). The results given in Table 3 show very fast response times, high polarizations, and low viscosities. In addition, the response times are relatively temperature-independent.

Example 45

A device was prepared and evaluated essentially as described in Example 36 using 100 weight percent 5-octyloxy-2-[4-((R)-2-fluoro-3-(2-(2-(nonafluorobutoxy) tetrafluoroethoxy)-2,2,-difluoroethoxy)propoxy)phenyl] pyrimidine (Example 10). The results given in Table 3 show very fast response times, high polarizations, low viscosities, and a very broad smectic C. temperature range. In addition, the response times are relatively temperature-independent.

Example 46

A device was prepared and evaluated essentially as described in Example 36 using 100 weight percent 5-((R)-2-fluorooctyloxy)-2-[4-((R)-2-fluoro-3-(2-(2-(nonafluorobutoxy)tetrafluoroethoxy)-2,2,-difluoroethoxy) propoxy)phenyl]pyrimidine (Example 18). The results given in Table 3 show very fast response times, high polarizations, and low viscosities.

Example 47

A device was prepared and evaluated essentially as described in Example 36 using 100 weight percent 5-((S)-2-fluorooctyloxy)-2-[4-((R)-2-fluoro-3-(2-(2-(nonafluorobutoxy)tetrafluoroethoxy)-2,2,-difluoroethoxy) propoxy)phenyl]pyrimidine (Example 19). The results given in Table 3 show very fast response times, high polarizations, and low viscosities.

Example 48

A device was prepared and evaluated essentially as described in Example 36 using a mixture of 10.2 weight percent N-(4-octyloxy)phenyl-(S)-5-((2-(2-(nonafluorobutoxy)tetrafluoroethoxy)-2,2-difluoroethoxy) methyl-2-oxazolidinone (Example 20), 59.9 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine, and 29.9 weight percent 5-octyl-2-[4-(2-(2-(nonafluorobutoxy)tetrafluoroethoxy)-2,2-difluoroethoxy) phenyl]pyrimidine. The results given in Table 3 show high polarizations at low chiral dopant concentration.

In addition, the phase transition temperatures of the mixture were measured essentially as described above and were found to be: I to A=93.7° C., A to C=41.9° C., and C to K=<-10° C.

Example 49

A device was prepared and evaluated essentially as described in Example 36 using 100 weight percent 5-hexyloxy-2-[4-((R)-2-fluoro-3-(2-(2-(nonafluorobutoxy)tetrafluoroethoxy)-2,2,-difluoroethoxy)propoxy)phenyl] pyrimidine (Example 9). The results given in Table 3 show very fast response times, high polarizations, low viscosities, and a very broad smectic C. temperature range. In addition, the response times are relatively temperature-independent.

Example 50

A device was prepared and evaluated essentially as described in Example 36 using a mixture of 5 weight percent 5-octyl-2-[4-((R)-2-fluoro-3-(2-(2-(nonafluorobutoxy) tetrafluoroethoxy)-2,2,-difluoroethoxy)propoxy)phenyl] pyrimidine (Example 5) and 95 weight percent 5-heptyl-2-[4-(2-(2-(pentaafluoroethoxy)tetrafluoroethoxy)-2,2,-difluoroethoxy)phenyl]pyrimidine (prepared essentially as described in U.S. Pat. No. 5,262,082 (Janulis et al.)). The results given in Table 3 show a low viscosity for the mixture, which provides a very fast response time in spite of the low polarization exhibited.

In addition, the phase transition temperatures of the mixture were measured essentially as described above and were found to be: I to A=84.2° C., A to C=53.0° C., C to K=8.4° C., and K to C=29.1° C.

Example 51

A device was prepared and evaluated essentially as described in Example 36 using 100 weight percent 5-octyl-2-[4-((R)-2-fluoro-3-(2-(2-(2-(trifluoromethoxy)tetrafluoroethoxy)tetrafluoroethoxy)-2,2,-difluoroethoxy) propoxy)phenyl]pyrimidine (Example 11). The results given in Table 3 show very fast response times, high polarizations, and low viscosities.

Example 52

A device was prepared and evaluated essentially as described in Example 36 using 100 weight percent 5-octyl-2-[4(nonafluorobutoxy)tetrafluoroethoxy-(2-(nonafluorobutoxy)tetrafluoroethoxy)-2,2,3,3,4,4,5,5,6,6,7,7,8,8,9,9,10,10-octadecafluorodecyloxy)propoxy)phenyl] pyrimidine (Example 13). The results given in Table 3 show a fast response time, a high polarization, and a low viscosity.

Example 53

A device was prepared and evaluated essentially as described in Example 36 using a mixture of 10 weight percent (S)-5-octyl-2-[4-(2-(2-(nonafluorobutoxy) tetrafluoroethoxy)-2,2-difluoroethoxy)methyl-2-oxazolidinone)phenyl]pyrimidine (Example 33), 60 weight percent 5-octyl-2-[4-(6-(2-(nonafluorobutoxy) tetrafluoroethoxy)-2,2,3,3,4,4,5,5,6,6-decafluorohexyloxy) phenyl]pyrimidine, and 30 weight percent 5-octyl-2-[4-(2-(2-(nonafluorobutoxy)tetrafluoroethoxy)-2,2-difluoroethoxy)phenyl]pyrimidine. The results given in Table 3 show high polarizations at low chiral dopant concentration.

In addition, the phase transition temperatures of the mixture were measured essentially as described above and were found to be: I to A=105.5° C., A to C=57.3° C., and C to K=16.4° C.

TABLE 3

|  | Reduced Temperature (T-T$_c$, °C.) | Polarization (nC/cm$^2$) | Response Time (μs) | Smectic Viscosity (mPa · s) | Tilt Angle (degrees) |
| --- | --- | --- | --- | --- | --- |
| Example 36 | −1.40 | 7.40 | 16 | 11.8 | 26.00 |
|  | −2.40 | 7.90 | 23 | 18.2 | 27.25 |
|  | −5.40 | 8.90 | 24 | 21.3 | 29.75 |
|  | −10.90 | 9.60 | 31 | 29.7 | 32.50 |
|  | −15.70 | 10.40 | 37 | 38.5 | 33.50 |
|  | −25.80 | 11.20 | 52 | 58.2 | 34.00 |
|  | −35.70 | 12.20 | 80 | 97.6 | 34.00 |
|  | −45.70 | 13.40 | 135 | 180.9 | 34.50 |
| Example 37 | −30.1 | 20.4 |  |  | 30.6 |
| Comparative Example 3 | −27.5 | 5.2 |  |  | 29.2 |
| Example 38 | −1 | 1.3 | 42 | 5.46 |  |
|  | −5 | 1.9 | 90 | 17.1 | 24 |
|  | −10 | 1.9 | 120 | 22.8 | 25.5 |
|  | −15 | 2.2 | 145 | 31.9 | 26.5 |
|  | −25 | 2.6 | 200 | 50.96 | 28.5 |
| Example 39 | −2 | 5.8 | 17 | 9.86 | 19 |
|  | −5 | 7.3 | 32 | 23.36 | 22 |
|  | −15 | 9.8 | 52 | 50.96 | 27.5 |
|  | −25 | 10.8 | 90 | 97.2 | 29 |
|  | −30 | 11.7 | 125 | 146.25 | 29.5 |
|  | −40 | 13 | 280 | 364.55 | 29.5 |
| Example 40 | −3.1 | 81.1 | 3.9 | 31.6 | 22.4 |
|  | −6.5 | 90.7 | 4.4 | 39.9 | 23.45 |
|  | −14 | 107.6 | 5.3 | 57.0 | 24.85 |
|  | −19.1 | 118.7 | 6.2 | 73.6 |  |
|  | −25.5 | 127.6 | 7.1 | 90.6 | 25.95 |
|  | −36.9 | 146.2 | 9.9 | 144.7 | 26.4 |
|  | −48.5 | 160.9 | 15 | 241.3 | 26.3 |
| Example 41 | −6.5 | 178 | 7.5 | 133.5 |  |
|  | −16.5 | 213 | 12.0 | 255.6 |  |
| Example 42 | −36.5 | 11 | 57 | 71.5 | 30.8 |
| Comparative Example 4 | −32.5 | 1.3 | infinite |  |  |
| Example 43 | −0.90 | 66.00 |  |  | 20.55 |
|  | −3.00 | 75.00 | 3.30 | 26.07 | 21.65 |
|  | −6.00 | 84.00 | 3.70 | 32.74 | 22.85 |
|  | −8.60 | 92.00 | 4.20 | 40.70 | 23.75 |
|  | −11.80 | 99.00 | 4.60 | 47.97 | 24.5 |
|  | −15.80 | 110.00 | 5.10 | 59.10 | 25.25 |
|  | −20.90 | 116.00 | 5.70 | 69.65 | 25.85 |
|  | −23.90 | 122.00 | 6.10 | 78.39 | 26.1 |
| Example 44 | −6.30 | 79.90 | 3.40 | 28.74 | 22.9 |
|  | −10.90 | 94.20 | 4.20 | 41.86 | 24.5 |
|  | −16.00 | 109.40 | 5.40 | 62.51 | 26.05 |
| Example 45 | −2.00 | 102.80 | 4.00 | 43.98 | 31.35 |
|  | −9.00 | 117.90 | 4.40 | 55.49 | 33.3 |
|  | −22.00 | 140.40 | 5.70 | 85.60 | 34.85 |
|  | −41.40 | 166.60 | 8.60 | 153.25 | 35.4 |
|  | −74.20 | 200.20 | 32.00 | 685.26 | 34.65 |
| Example 46 | −0.90 | 70.90 | 6.00 | 45.54 | 30.45 |
|  | −6.70 | 92.20 | 7.00 | 69.10 | 33.45 |
|  | −21.30 | 84.80 | 14.00 | 127.10 | 35.4 |

TABLE 3-continued

| | Reduced Temperature (T-T$_c$, °C.) | Polarization (nC/cm$^2$) | Response Time (μs) | Smectic Viscosity (mPa · s) | Tilt Angle (degrees) |
|---|---|---|---|---|---|
| Example 47 | −1.00 | 133.40 | 7.50 | 105.74 | 34.05 |
| | −5.40 | 155.80 | 8.10 | 133.37 | 34.65 |
| | −9.60 | 178.50 | 8.50 | 160.35 | 34.7 |
| Example 48 | −4.00 | 42.30 | 8.90 | 37.65 | 49.10 |
| | −12.30 | 52.60 | 13.30 | 69.96 | 54.50 |
| | −20.40 | 60.10 | 19.40 | 116.59 | 57.20 |
| | −28.50 | 65.70 | 30.80 | 202.36 | 58.70 |
| | −36.90 | 68.90 | 54.80 | 377.57 | 59.50 |
| | −45.10 | 72.00 | 110.00 | 792.00 | 59.90 |
| Example 49 | −7.40 | 96.00 | 3.70 | 35.52 | 28.35 |
| | −20.80 | 122.30 | 4.70 | 57.48 | 31.35 |
| | −37.50 | 149.90 | 6.10 | 91.44 | 32.55 |
| | −67.10 | 195.20 | 13.70 | 267.42 | 32.60 |
| Example 50 | −2.20 | 7.40 | | | 13.25 |
| | −3.90 | 8.50 | | | 16.7 |
| | −6.90 | 12.30 | 6.80 | 8.36 | 18.55 |
| | −10.00 | 13.90 | 9.30 | 12.93 | |
| | −11.90 | 14.40 | 10.70 | 15.41 | 20.4 |
| | −13.90 | 15.70 | 11.60 | 18.21 | 20.85 |
| | −20.20 | 18.00 | 14.70 | 26.46 | 20.05 |
| | −25.00 | 19.30 | 18.20 | 35.13 | 22.8 |
| Example 51 | −5.00 | 88.00 | 4.20 | 36.96 | 22.75 |
| | −20.90 | 110.70 | 6.20 | 68.63 | 24.4 |
| Example 52 | −3.00 | 77.20 | 6.40 | 49.41 | 0 |
| Example 53 | 0 | 30.7 | 3 | 9.21 | 17 |
| | −5 | 44.2 | 6 | 26.52 | 23.5 |
| | −15 | 55.8 | 9.5 | 53.01 | 28 |
| | −20 | 59.5 | 11.5 | 68.425 | 28.5 |
| | −30 | 65.9 | 19 | 125.21 | 29 |
| | −40 | 68.5 | 36 | 246.6 | 29 |

Various modifications and alterations of this invention will become apparent to those skilled in the art without departing from the scope and spirit of this invention.

We claim:

1. Fluorine-containing, chiral liquid crystal compounds that have smectic mesophases or latent smectic mesophases and that are represented by the general formula (I):

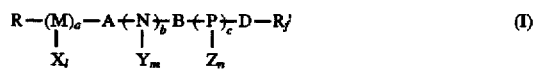

where M, N, and P are each independently selected from the group consisting of

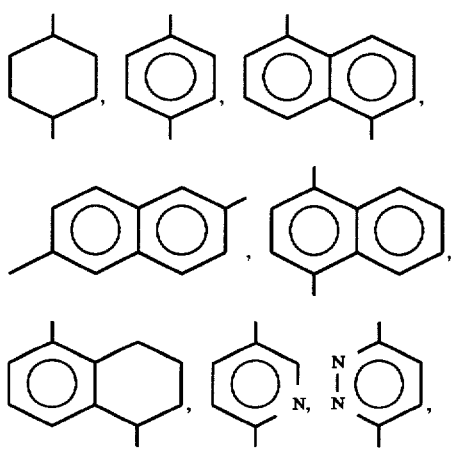

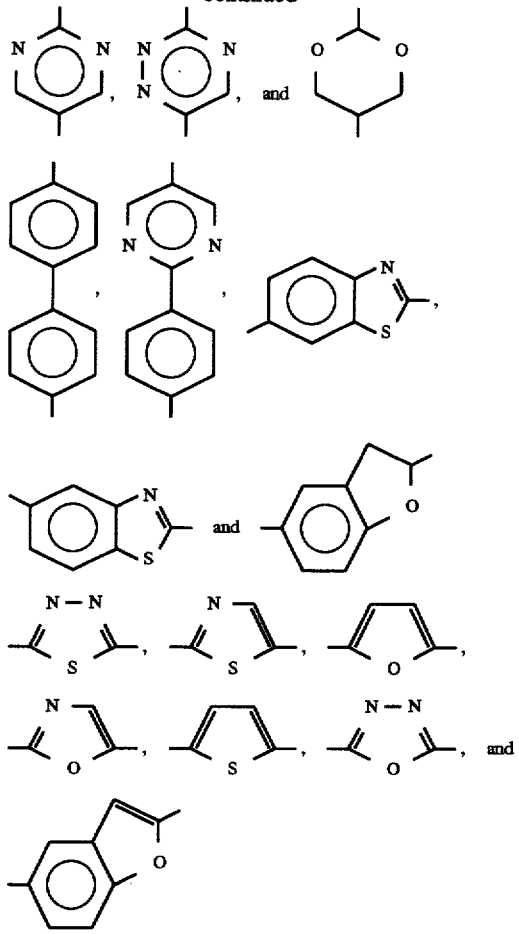

a, b, and c are each independently zero or an integer of from 1 to 3, with the proviso that the sum of a+b+c be at least 1;

each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$ where K is 1 to 4, —CH=CH—, —C≡C—, —CH=N—, —CH$_2$—O—,
—C(=O)—, and —O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

D is non-directionally selected from the group consisting of a covalent bond,

—C(=O)—O—C$_r$H$_{2r}$—, —O—C$_r$H$_{2r}$—,

—O—(O=)C—C$_r$H$_{2r}$—, —C≡C—,

-continued

—CH=CH—, —C(=O)—,

—O—(C$_r$H$_{2r}$O)$_s$—C$_t$H$_{2t'}$—, —C$_r$H$_{2r}$—,

—(C$_r$H$_{2r}$O)$_s$—C$_t$H$_{2t'}$—, —O—, —S—,

—OSO$_2$—, —SO$_2$—, —SO$_2$—C$_r$H$_{2r}$—,

—C$_r$H$_{2r}$—N—SO$_2$—, —N(C$_p$H$_{2p+1}$)—,
         |
         C$_p$H$_{2p+1}$

—C$_r$H$_{2r}$—N—C(=O)—, —CH=N—,
         |
         C$_p$H$_{2p+1}$ and combinations thereof, where r and r' are independently integers of 0 to about 20, s is independently an integer of 1 to about 10 for each (C$_r$H$_{2r}$O), t is an integer of 1 to about 6, and p is an integer of 0 to about 4;

R is selected from the group consisting of

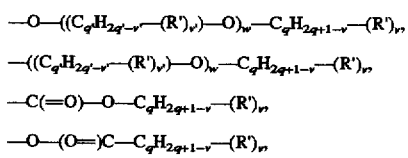

—C(=O)—O—C$_q$H$_{2q+1-v}$—(R')$_v$,

—O—(O=)C—C$_q$H$_{2q+1-v}$—(R')$_v$,

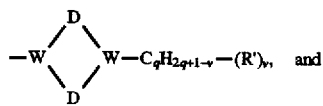

—CR'H—(D)$_s$—CR'H—C$_q$H$_{2q+1-v}$—(R')$_v$, where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$;

q' is independently an integer of 1 to about 20 for each (C$_q$H$_{2q}$—O); q is an integer of 1 to about 20; w is an integer of 0 to about 10; v is an integer of 0 to about 6; each v' is independently an integer of 0 to about 6; g is an integer of 1 to about 3; each D is independently and non-directionally selected from the group set forth for D above, with the proviso that the ring containing D has from about 3 to about 10 ring atoms; each W is independently selected from the group consisting of N, CR', and SiR'; and R is chiral or achiral; and R$_f'$ is —R*—D—(O)$_x$—CH$_2$—D'—R$_f$, where R* is a cyclic or acyclic chiral moiety selected from the group consisting of

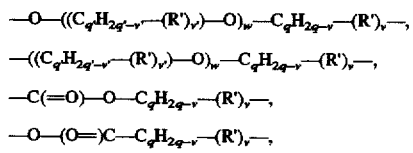

—C(=O)—O—C$_q$H$_{2q-v}$—(R')$_v$—,

—O—(O=)C—C$_q$H$_{2q-v}$—(R')$_v$—,

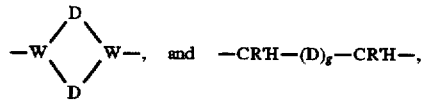

where each R' is —F; q' is independently an integer of 1 to about 20 for each (C$_q$H$_{2q}$—O); q is an integer of 1 to about 20; w is an integer of 0 to about 10; v is an integer of 1 to about 3; each v' is independently an integer of 0 to about 6; g is an integer of 1 to about 3; each D is independently and non-directionally selected from the group set forth for D above, with the proviso that the ring containing D has from about 3 to about 10 ring atoms; each W is independently selected from the group consisting of N and CH; and with the proviso that R* is chiral; D and D' are each independently and non-directionally selected from the group set forth for D above; x is an integer of 0 or 1; and R$_f$ is fluoroalkyl, perfluoroalkyl, fluoroether, or perfluoroether.

2. Fluorine-containing, chiral liquid crystal compounds that have smectic mesophase or latent smectic mesophase and that are represented by the general formula (II):

R''—(O)$_j$—G—(OCH$_2$)$_j$—R*—(C$_x$H$_{2x}$O)$_z$H$_{2y}$—R$_f$    (II)

where R'' is (R')$_v$—C$_q$H$_{2q+1-v}$, where q is an integer of 2 to about 10, each R' is independently selected from the group consisting of hydrogen, fluorine, chlorine, methyl, and perfluoromethyl, and v is an integer of 1 to about 3; j is an integer of 0 or 1; G is selected from the group consisting of

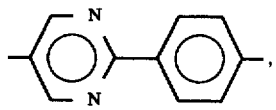

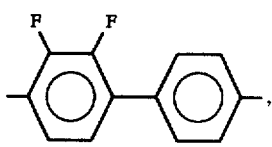

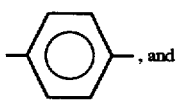, and

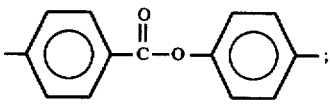

R* is selected from the group consisting of —C$_q$H$_{2q-v}$—(R')$_v$— and

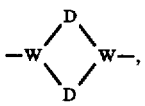

where R' is —F, q is an integer of 1 to about 4, v is an integer of 1 to about 3, W is N or CH, and D is a cyclic or acyclic chiral moiety —C(=O)—O— or —CH$_2$—; s is an integer of 1 to about 6; t is an integer of 0 or 1; r' is an integer of 1 to about 3; and R$_f$ is selected from the group consisting of —C$_q$F$_{2q}$X', —R$_f''$—R$_h$, and —(C$_x$F$_{2x}$O)$_z$C$_y$F$_{2y+1}$, where q is an integer of 1 to about 6, X' is fluorine, R$_f''$ is a linear or branched, perfluorinated alkylene group having from about 2 to about 4 carbon atoms and optionally containing one or more catenary ether oxygen atoms, R$_h$ is a linear or branched alkyl group having from about 2 to about 7 carbon atoms and optionally containing one or more catenary ether oxygen atoms, x is independently an integer of i to about 10 for each (C$_x$F$_{2x}$O), y is an integer of 1 to about 8, and z is an integer of 1 to about 5.

* * * * *

UNITED STATES PATENT AND TRADEMARK OFFICE
CERTIFICATE OF CORRECTION

PATENT NO. : 5,702,637
DATED : December 30, 1997
INVENTOR(S) : Gilbert C. Johnson et al.

It is certified that error appears in the above-identified patent and that said Letters Patent is hereby corrected as shown below:

Column 4,
Line 44, delete "$(C_sH_{2s O})_t C_{r'} H_{2r'}$" and insert therefore -- $(C_s H_{2s} O)_t C_{r'} H_{2r'}$ --.
Line 62, delete "-- $((C_{q'} H_{2q'-v'}-(R')_{v'})\text{-}O)_w-C_q H_{2q+1-v}-(R')_v$," and insert therefore
-- -- $((C_{q'} H_{2q'-v'}-(R')_{v'})\text{-}O)_w-C_q H_{2q+1-v}-(R')_v$ , --.

Column 5,
Line 14, delete "$-H_q H_{2q+1}$," and insert therefore -- $-C_q H_{2q+1}$, --.

Column 7,
Line 41, delete "$R_r'$ " and insert -- $R_f'$ --.

Column 28,
Line 43, delete "(2butoxyethoxy)" and insert therefore -- (2-butoxyethoxy) --.

Column 33,
Line 56, delete "[4(nonafluorobutoxy) tetrafluoroethoxy-" and insert therefore
-- [4-((R)-2-fluoro-3-(10-(2-(nonafluorobutoxy) tetrafluoroethoxy)- --.

Column 36,
Line 46, "-- $(CH_2CH_2)_k$" should read -- -- $(CH_2CH_2)_k$-- --.

Column 38,
Line 14, delete "mesophase" (both instances) and insert therefore -- mesophases --.
Line 43, after "is" insert therefore -- a cyclic or acyclic chiral moiety --.
Lines 52-53, delete "a cyclic or acyclic chiral moiety".
Line 63, delete "i" insert therefore -- 1 --.

Signed and Sealed this

Fourth Day of June, 2002

*Attest:*

*Attesting Officer*

JAMES E. ROGAN
*Director of the United States Patent and Trademark Office*